(12) United States Patent
Anderson et al.

(10) Patent No.: US 11,844,956 B2
(45) Date of Patent: Dec. 19, 2023

(54) IMMERSIVE, FLUX-GUIDED, MICRO-COIL APPARATUS AND METHOD

(71) Applicant: PULSE, LLC, Draper, UT (US)

(72) Inventors: Gregory S. Anderson, Sandy, UT (US); Kade E. Huntsman, Holladay, UT (US); Dale C. Gledhill, Sandy, UT (US); Douglas R. Burrell, Springville, UT (US)

(73) Assignee: PULSE, LLC, Draper, UT (US)

( * ) Notice: Subject to any disclaimer, the term of this patent is extended or adjusted under 35 U.S.C. 154(b) by 579 days.

(21) Appl. No.: 16/715,153

(22) Filed: Dec. 16, 2019

(65) Prior Publication Data

US 2020/0360710 A1   Nov. 19, 2020

Related U.S. Application Data

(60) Division of application No. 14/276,172, filed on May 13, 2014, now Pat. No. 10,507,333, which is a continuation-in-part of application No. 13/890,798, filed on May 9, 2013, now abandoned, which is a continuation of application No. 12/502,998, filed on Jul. 14, 2009, now Pat. No. 8,439,816.

(51) Int. Cl.
*A61N 2/00* (2006.01)
*A61N 2/02* (2006.01)
*A61F 5/01* (2006.01)

(52) U.S. Cl.
CPC ............... *A61N 2/004* (2013.01); *A61N 2/02* (2013.01); *A61F 5/0106* (2013.01); *A61F 5/0111* (2013.01); *Y10T 29/49117* (2015.01)

(58) Field of Classification Search
CPC ..... A61N 2/004; A61N 2/02; Y10T 29/49117; A61F 5/0106; A61F 5/0111; A61F 5/0102; A61F 5/0109
See application file for complete search history.

(56) References Cited

U.S. PATENT DOCUMENTS 4,105,017 A   8/1978   Ryaby et al.
4,266,533 A   5/1981   Ryaby et al.
(Continued)

OTHER PUBLICATIONS

Advanced Biomagentics® Clinical Database: Osteoporosis Studies, therion®, J. Bone Joint Surg. Am.m http://www.therionresearch.com/database/osteoporosis.html#2, Mar. 1989;71(3):411-7.
(Continued)

*Primary Examiner* — Christine H Matthews
*Assistant Examiner* — Joshua Daryl D Lannu
(74) *Attorney, Agent, or Firm* — Pate Nelson & Hill, PLLC

(57) ABSTRACT

A pulsed electromagnetic field (PEMF) web using immersive, flux-guided, micro-coils to direct intense, deeply penetrating, magnetic flux into a subject from each micro-coil capable of pointing in an arbitrary direction. Micro-coils are spooled around iron cores, insulated properly, and soldered to connecting wires, all embedded in a polymeric resin, such as cold-cured silicone resin. Nodes protect, enclose, insulate electrically, and otherwise protect the micro-coils. Connectors between nodes provide mechanical stability against breaking of wires, while permitting folding, bending, buckling, and otherwise deflecting to position the nodes as desired with three degrees of freedom.

20 Claims, 16 Drawing Sheets

(56) References Cited

U.S. PATENT DOCUMENTS

| | | | |
|---|---|---|---|
| 4,315,503 A | 2/1982 | Ryaby et al. | |
| 4,510,704 A | 4/1985 | Johnson | |
| 5,014,699 A | 5/1991 | Pollack et al. | |
| 5,058,582 A | 10/1991 | Thaler | |
| 5,087,336 A | 2/1992 | Liboff et al. | |
| 5,160,591 A | 11/1992 | Liboff et al. | |
| 5,181,902 A | 1/1993 | Erickson et al. | |
| 5,269,745 A | 12/1993 | Liboff et al. | |
| 5,269,747 A | 12/1993 | Erickson et al. | |
| 5,290,409 A | 3/1994 | Liboff et al. | |
| 5,314,400 A | 5/1994 | Tsyb et al. | |
| 5,338,286 A | 8/1994 | Abbott et al. | |
| 5,344,384 A * | 9/1994 | Ostrow | A61N 2/02 600/13 |
| 5,370,133 A | 12/1994 | Darby et al. | |
| 5,458,558 A | 10/1995 | Liboff et al. | |
| 5,554,835 A | 9/1996 | Newham | |
| 5,654,694 A | 8/1997 | Newham | |
| 5,743,844 A | 4/1998 | Tepper et al. | |
| 5,792,209 A | 8/1998 | Varner | |
| 5,951,459 A | 9/1999 | Blackwell | |
| 5,997,464 A | 12/1999 | Blackwell | |
| 6,024,691 A | 2/2000 | Tepper et al. | |
| 6,132,362 A * | 10/2000 | Tepper | A61N 2/02 607/2 |
| 6,174,276 B1 | 1/2001 | Blackwell | |
| 6,179,772 B1 | 1/2001 | Blackwell | |
| 6,186,941 B1 | 2/2001 | Blackwell | |
| 6,200,259 B1 | 3/2001 | March | |
| 6,213,934 B1 | 4/2001 | Bianco et al. | |
| 6,261,221 B1 | 7/2001 | Tepper et al. | |
| 6,364,824 B1 | 4/2002 | Fitzsimmons | |
| 6,395,799 B1 | 5/2002 | Johnson | |
| 6,418,345 B1 | 7/2002 | Tepper et al. | |
| 6,443,883 B1 | 9/2002 | Ostrow et al. | |
| 6,463,336 B1 | 10/2002 | Mawhinney | |
| 6,560,487 B1 | 5/2003 | McGraw et al. | |
| 6,561,968 B1 | 5/2003 | Dissing et al. | |
| 6,589,194 B1 | 7/2003 | Calderon et al. | |
| 6,675,048 B2 | 1/2004 | McGraw et al. | |
| 6,792,315 B2 | 9/2004 | Carter et al. | |
| 6,819,210 B2 | 11/2004 | Boynton et al. | |
| 6,839,595 B2 | 1/2005 | Tepper et al. | |
| 6,853,863 B2 | 2/2005 | Carter et al. | |
| 6,853,864 B2 | 2/2005 | Litovitz | |
| 6,955,642 B1 | 10/2005 | Simon | |
| 7,010,353 B2 | 3/2006 | Gan et al. | |
| 7,130,692 B2 | 10/2006 | Brighton et al. | |
| 7,158,835 B2 | 1/2007 | Brighton et al. | |
| 7,175,587 B2 | 2/2007 | Gordon et al. | |
| D645,153 S | 9/2011 | Anderson et al. | |
| 8,147,395 B2 | 4/2012 | Anderson et al. | |
| D662,598 S | 6/2012 | Anderson et al. | |
| 8,439,816 B2 | 5/2013 | Anderson et al. | |
| 8,485,960 B2 | 7/2013 | Anderson et al. | |
| 2002/0151759 A1 | 10/2002 | Paturu | |
| 2002/0165583 A1 | 11/2002 | Tepper et al. | |
| 2003/0095022 A1 | 5/2003 | Boynton et al. | |
| 2003/0158585 A1 | 8/2003 | Burnett | |
| 2004/0210254 A1 | 10/2004 | Burnett | |
| 2005/0124846 A1 | 6/2005 | Pasula | |
| 2005/0182287 A1 | 8/2005 | Becker | |
| 2005/0267355 A1 | 12/2005 | Parker | |
| 2006/0212077 A1 | 9/2006 | Pilla et al. | |
| 2007/0293798 A1 | 12/2007 | Hu et al. | |

OTHER PUBLICATIONS

An Electrical Device to Make Bones Grow, http://www.thirdage.com/ebsco/files/14707.html, Medicinal EMFs: Harnessing electric and magnetic fields for healing and health, Science News Online, http://wwwl.sciencenews.org/sn_arc99/11_13_99/bob2.htm, Apr. 19, 2011.

Data providing the effect of electrical field stimulation on BMD and BMC, http://www.scielo.br/scielo.php?pid=S0100-879X2006005000030&script=sci_arttext, Apr. 19, 2011.

Pulsed Electromagnetic Fields for Bone Health and Bone Healing, QRS World of Health, http://www.qrsworldofhealth.com/osteoporosis_intro.html, Mar. 12, 2008.

Hiromasa Miura, Application of a Pulsed Electromagnetic Field for the Treatment of Osteoporosis, Department of Orthopaedic Surgery, Kyushu University, Apr. 19, 2011.

Kyle Chang, Walter Hong-Shong Chang, Yen-Hsin Yu, Chung Shih, Pulsed Eectromagnetic Field Stimulation of Bone Marrow Cells Derived from Ovariectomized Rats Affects Osteoclast Formation and Local Factor Production, May 14, 2003, (Abstract Only), http://www3.interscience.wiley.com/search/allsearch?mode=viewselected&product=journal&ID=107061128&view_selected.x=69&view_selected.y=9.

Jitendra Behari and Jayanand, Low Level Pulsed Radio Frequency Field and Its Remedial Effect on Osteoporosis and Bone Fracture, Progress in Electromagnetics Research Symposium 2005, Aug. 22-26, 2005, pp. 736-739 Hangzhou, China.

Lirani-Galvãão, C.T. Bergamaschi, O.L. Silva and M. Lazaretti-Castro, Electrical Field Stimulation Improves Bone Mineral Density in Ovariectomized Rats, Brazilian Journal of Medical and Biological Research, Nov. 2006, 1501-1505; http://www.scielo.br/pdf/bjmbr/v39n11/6295.pdf.

Paul Andrew Glazer, Lian Clamen Glazer "Electricity: The History and Science of Bone Growth Stimulation for Spinal Fusion." Orthopaedic Journal at Harvard Medical School. http://www.orthojournalhms.org/ojhms2002/manuscripts/manuscripts-01.htm. Mar. 12, 2009.

Daodaor Technologies Limited, "A New Idea on the Magnetic Products," 258 Zhonghe Zhong Road, Hangzhou, 310003, Phone: 86-571-86559319; 4 pages; May 4, 2010.

* cited by examiner

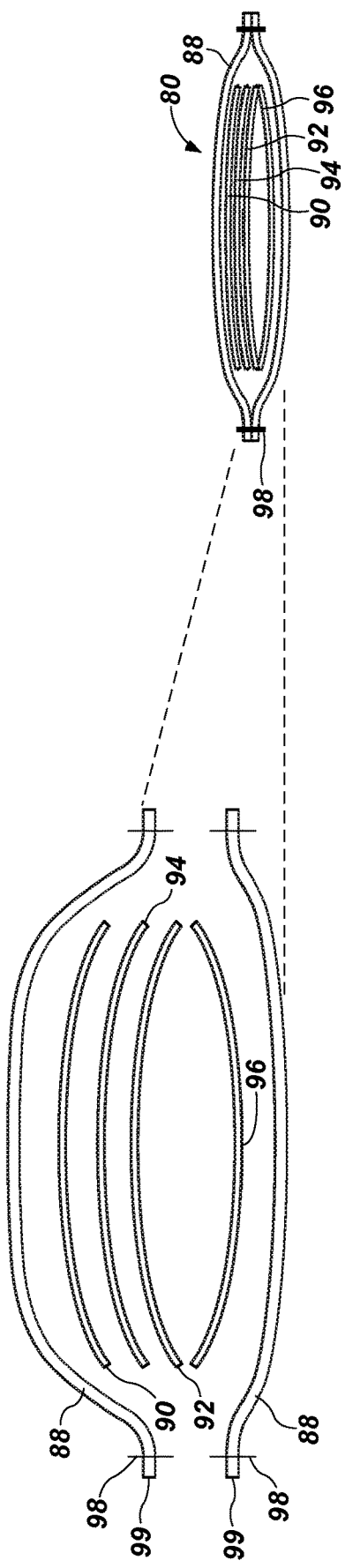
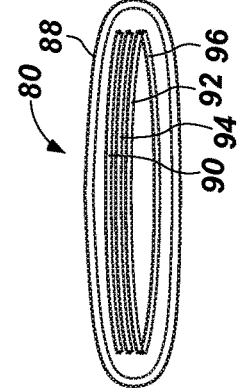
FIG. 19
FIG. 20
FIG. 21

IMMERSIVE, FLUX-GUIDED, MICRO-COIL APPARATUS AND METHOD

RELATED APPLICATIONS

This application: is a divisional (continuation) of U.S. patent application Ser. No. 14/276,172, filed May 13, 2014, entitled IMMERSIVE, FLUX-GUIDED, MICRO-COIL APPARATUS AND METHOD, scheduled to issue as U.S. Pat. No. 10,507,333 on Dec. 17, 2019, which is a continuation-in-part of co-pending U.S. patent application Ser. No. 13/890,798, filed May 9, 2013, entitled PIEZOELECTRIC, MICRO-EXERCISE APPARATUS AND METHOD, which is a continuation of U.S. patent application Ser. No. 12/502,998, filed Jul. 14, 2009, issued on May 14, 2013 as U.S. Pat. No. 8,439,816, entitled PIEZOELECTRIC, MICRO-EXERCISE APPARATUS AND METHOD, all of which are hereby incorporated herein by reference.

BACKGROUND

1. Field of the Invention

This invention relates to pulsed electromagnetic fields (PEMF) and, more particularly, to novel systems and methods for configuring magnetic coils, a matrix for those coils, and flux guiding by using iron-core magnets.

2. Background Art

Bones represent a curious structure, often referred to in the prior art as "not well understood." In space, such as during missions to the moon, extended orbits, work within a space station, normal loading (forces) is absent. Likewise, during healing of a broken arm or leg immobilized in a cast for typically six weeks or more, and the like, bone and soft tissue are lost. In these situations, people of science have studied the loss of cellular mass. The lack of exercise appears to relate to the loss of muscle and bone mass. For example, soft tissue, like muscle, atrophies without the stress of use. Mass loss is marked after a period of weightlessness, inactivity, non-weight bearing, immobility, or the like. Inactivity also exacerbates certain diseases, like arthritis. Moreover, bone mass may be lost at a greater rate in the absence of exercise then it can typically be regained upon resumption of exercise.

What is needed is an apparatus and method to apply exercise to a bone structure, soft tissues, or both that may be immobilized or subject to atrophy as a result of casting, traction, immobilization, malnourishment, diabetic or other circulation limitations, aging, or the like. Thus, what is needed is a system and method for applying this information into therapies and devices suitable for use in mammals, including persons, their pets, or both.

BRIEF SUMMARY OF THE INVENTION

In view of the foregoing, in accordance with the invention as embodied and broadly described herein, a method and apparatus are disclosed in one embodiment of the present invention as including a web that frees up a group of micro-coil, electromagnetic, devices to be positioned in a conformal shape suitable for surrounding an appendage, conforming to any part of the body, use in a bed, inclusion in a pad or blanket, or the like.

It has been found recently that application of PEMF systems in accordance with the invention are not only effective for maintaining bone density, assisting in non-joinder fracture recovery, and so forth with additional benefits. For example, it has been found that the use of PEMF systems in accordance with Applicants' inventions, after extensive periods of immobility and non-weight-bearing conditions required for bone healing, renders the typical muscular atrophy absent. After being cast for over six weeks, soft tissue tone and mass has been indistinguishable from that of the opposite, unaffected appendage.

Many advantages have been found for a new configuration of matrix for holding coils, and the use of iron-cored micro-coils. For example, the system may be placed in any arbitrary shape, providing three degrees of freedom for arrangement of the direction and the position of various micro-coil based electromagnets. The web is made of nodes connected by various connectors.

The connectors provide mechanical connection between the nodes. They also embed therewithin electrical connections. Iron cores provide greater magnetic power to the micro-coil magnets. One benefit of the molded, flexible, sparse web is a prevention of damage to connecting wires, by several mechanisms.

For example, one method relies on open molding or casting the connectors. They may be from about half a centimeter to about one and one half centimeters in effective diameter. A target range is about one centimeter in effective diameter. The embedded wires therein are automatically radiused in bending to prevent kinking, high stress, and other factors that tend to break wires. Moreover, the wires are stranded, thus becoming much more flexible. Typically, stranded wires of about 22 gauge have been found suitable, and are used with conventional plastic insulation.

Likewise, the entire circuit is thereby embedded within the web in order to power a group of from about 15 to about 60 or more nodes containing electromagnetic micro-coils. Typically, a number of nodes on the order of from about 10 to about 60 micro-coils in a web has been found suitable. The web may be rolled, folded, or the like for storage. Connectors are very flexible. Meanwhile, the web may be wrapped, distorted, secured, positioned, or otherwise located such that the individual micro-coils are directed at a particular bodily member from several directions.

In certain presently contemplated embodiments, all the micro-coils are connected in a single, series circuit. In this way, a controller simply controls one circuit, and all magnets are cycled with pulsed electromagnetic forces being generated simultaneously. However, since they are at a significant distance from one another, and having iron cores as flux guides, their electromagnetic field or force tends to be concentrated and directed. It saturates through the bodily member at which the particular core and associated micro-coil are directed.

Interference of coils with one another is not a significant difficulty. This is in contrast to prior attempts where no iron cores are used, large flat "mats" or "race tracks" of coils are used, and so forth. Thus, in general, PEMF systems typically will rely on large expanses with the lines of magnetic flux passing through the coils and immediately distributing out and away from each other and the central region of the coil.

In contrast, apparatus and methods in accordance with the invention concentrate flux in iron cores (inside micro-coils) that are then able to direct and project those electromagnetic fields well into the treated tissues.

The several micro-coils within a web may be arranged in an arbitrary orientation in multiple directions, including all three degrees of freedom. Moreover, various micro-coils may be simultaneously and arbitrarily aimed by positioning the flux directors, which direct flux perpendicular to the flat face of a node (appearing something like a small hockey puck) at the junction of associated connectors.

Mechanically, the web has a certain selective stability. In one embodiment, the web may be formed of triangles in order to position the micro-coils inside a more-or-less hexagonal perimeter. Individual nodes may be connected to other nodes by connectors, which may be easily folded, distorted, or otherwise buckled in bending, compression, or both in order to move them about.

Meanwhile, the cross-section of each of the connectors is selected to support tension at a value sufficient that the wires are not stretched. Thus, a certain amount of selective stability is provided wherein the web may be concentrated, folded, bent, and wrapped, but not stretched appreciably. The result is an immersive, flux-guided, system of micro-coils suitable for pulsed electromagnetic field therapy.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 19 is a cross-sectional view of one embodiment of a switch capable of detecting the presence of a user, and operating the system in response to that presence;

FIG. 20 is a cross-sectional view of an alternative embodiment thereof;

FIG. 21 is a cross-sectional view of an alternative embodiment thereof;

DETAILED DESCRIPTION OF THE PREFERRED EMBODIMENTS

Figure 1:
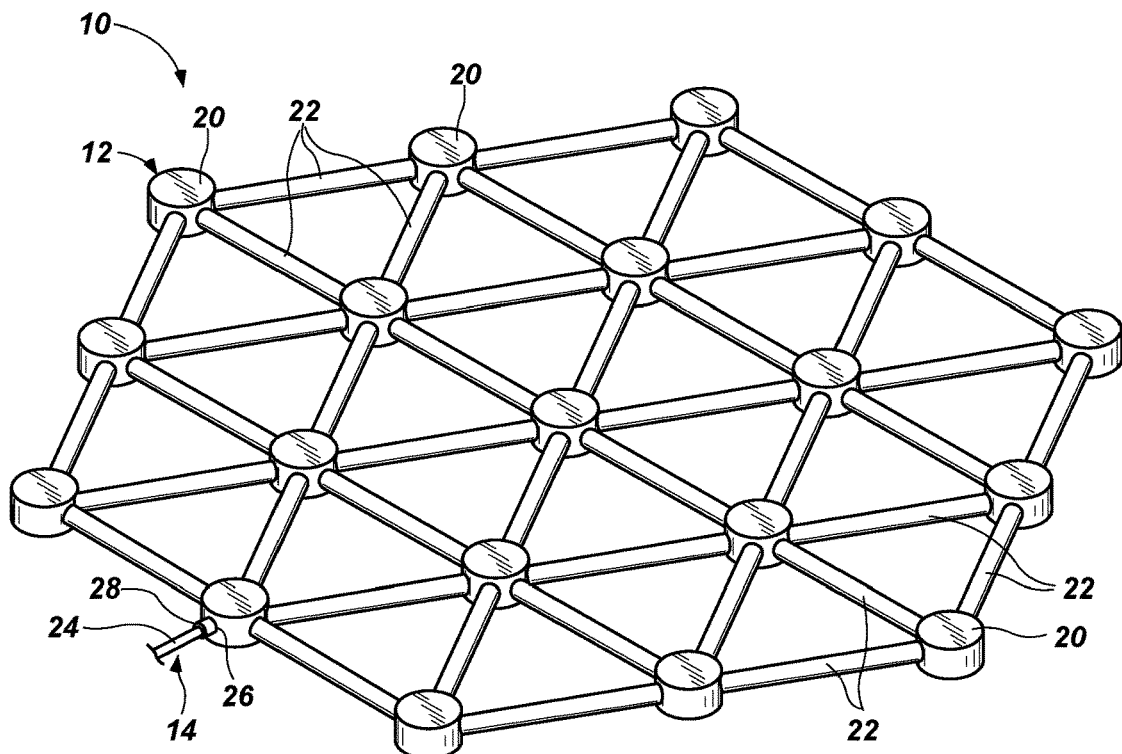
FIG. 1 is top perspective view of one embodiment of a PEMF web system in accordance with the invention.
Figure 2:
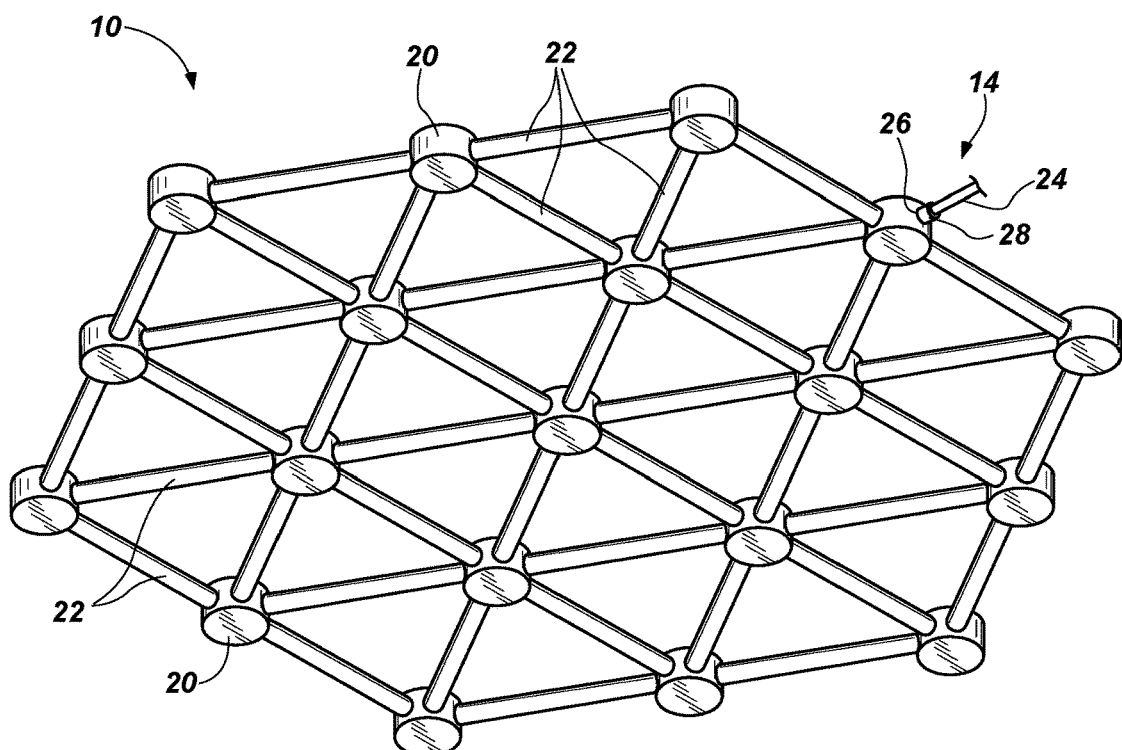
FIG. 2 is a bottom perspective view thereof.
Figure 3:
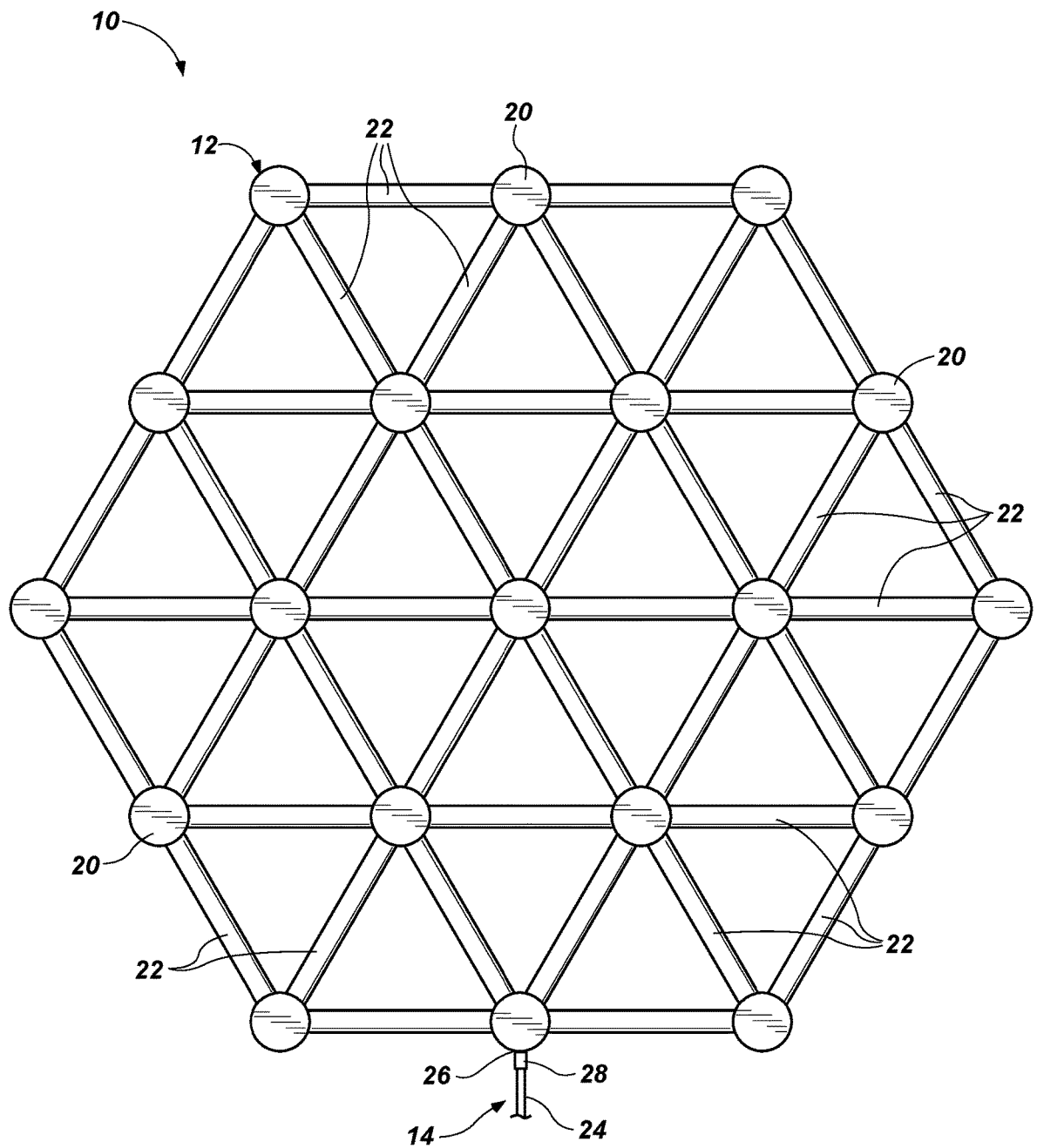
FIG. 3 is a top plan view thereof.
Figure 4:
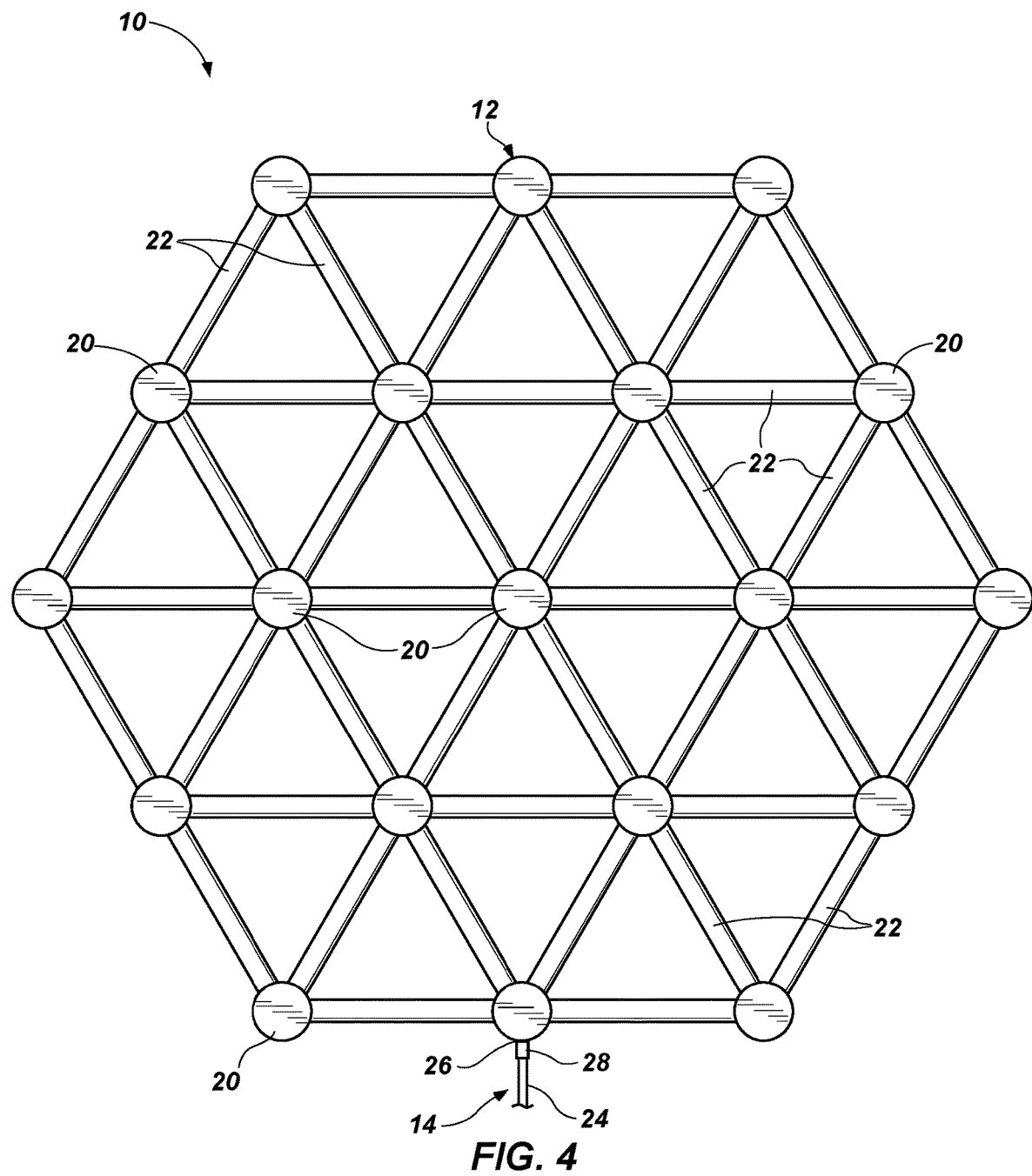
FIG. 4 is a bottom plan view thereof.
Figure 5:
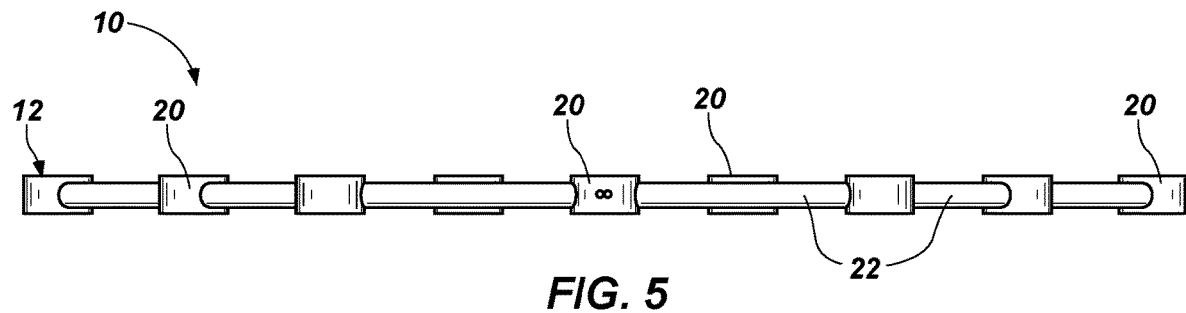
FIG. 5 is a front elevation view thereof.
Figure 6:
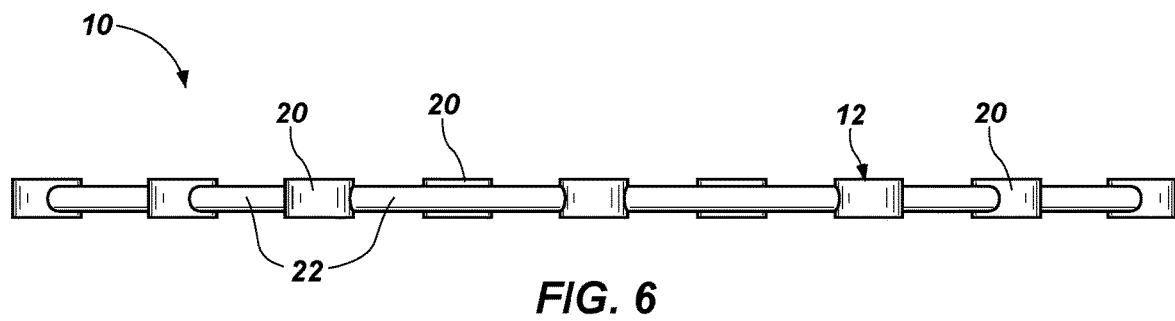
FIG. 6 is a rear elevation view thereof.
Figure 7:
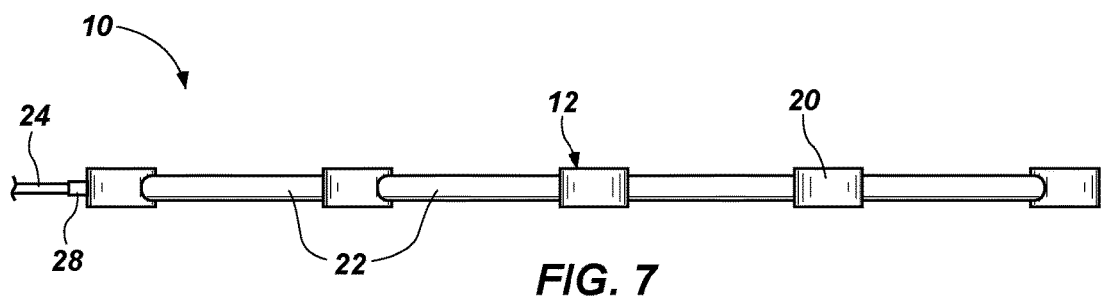
FIG. 7 is a right side elevation view thereof.
Figure 8:
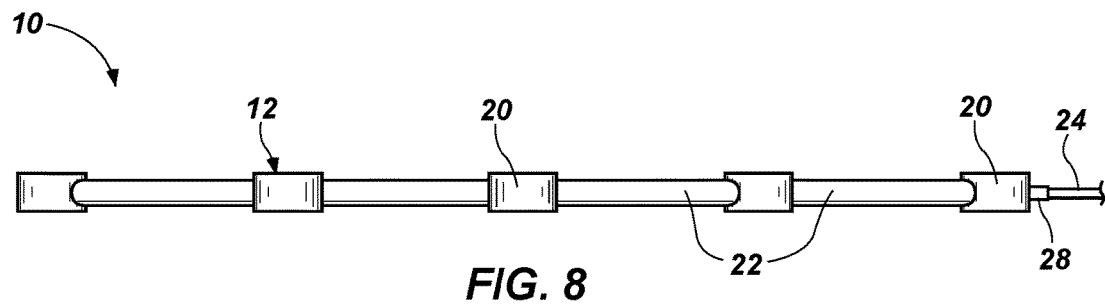
FIG. 8 is a left side elevation view thereof.
Figure 9:
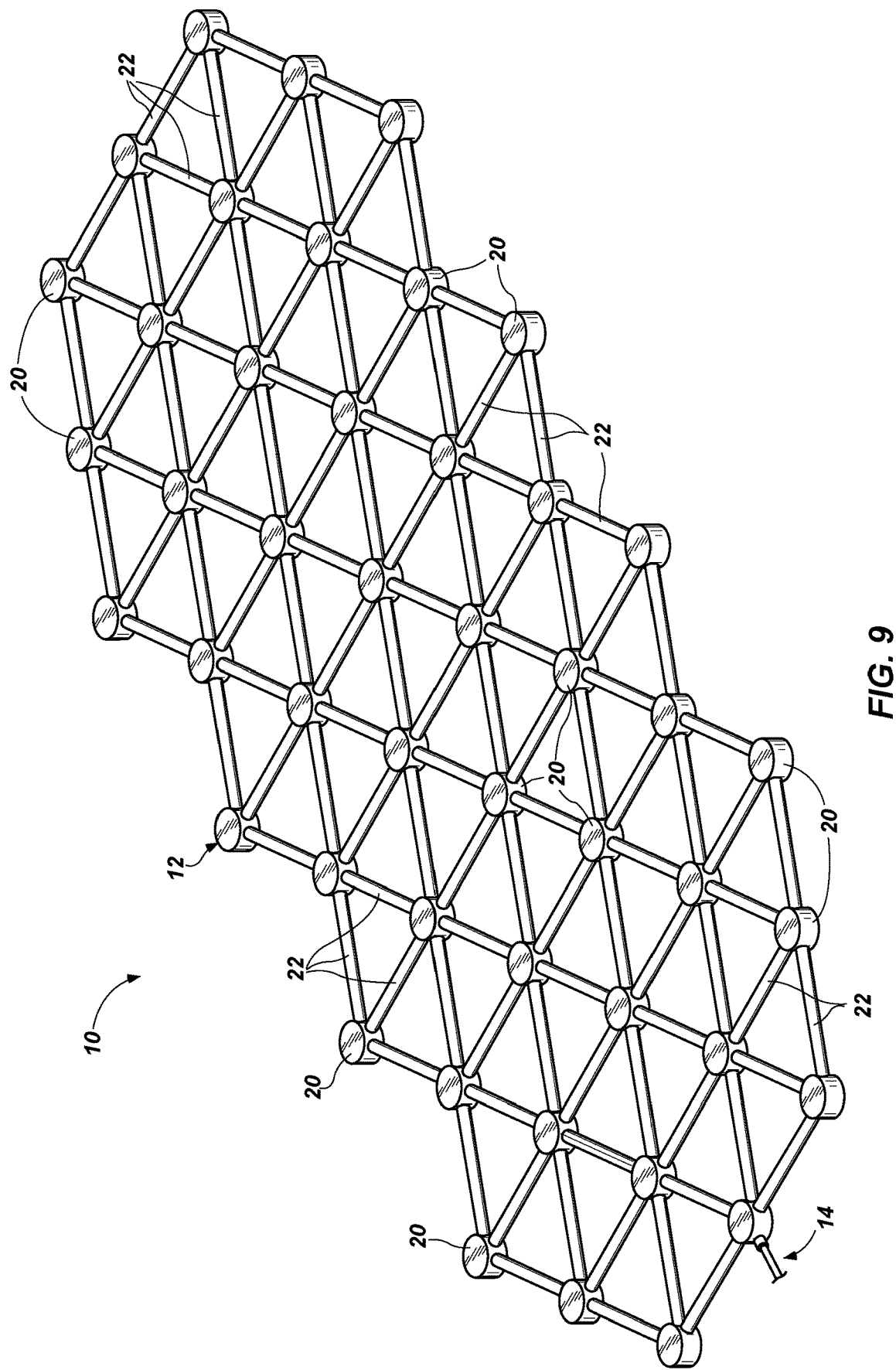
FIG. 9 is a top perspective view of an extended embodiment thereof.
Figure 10:
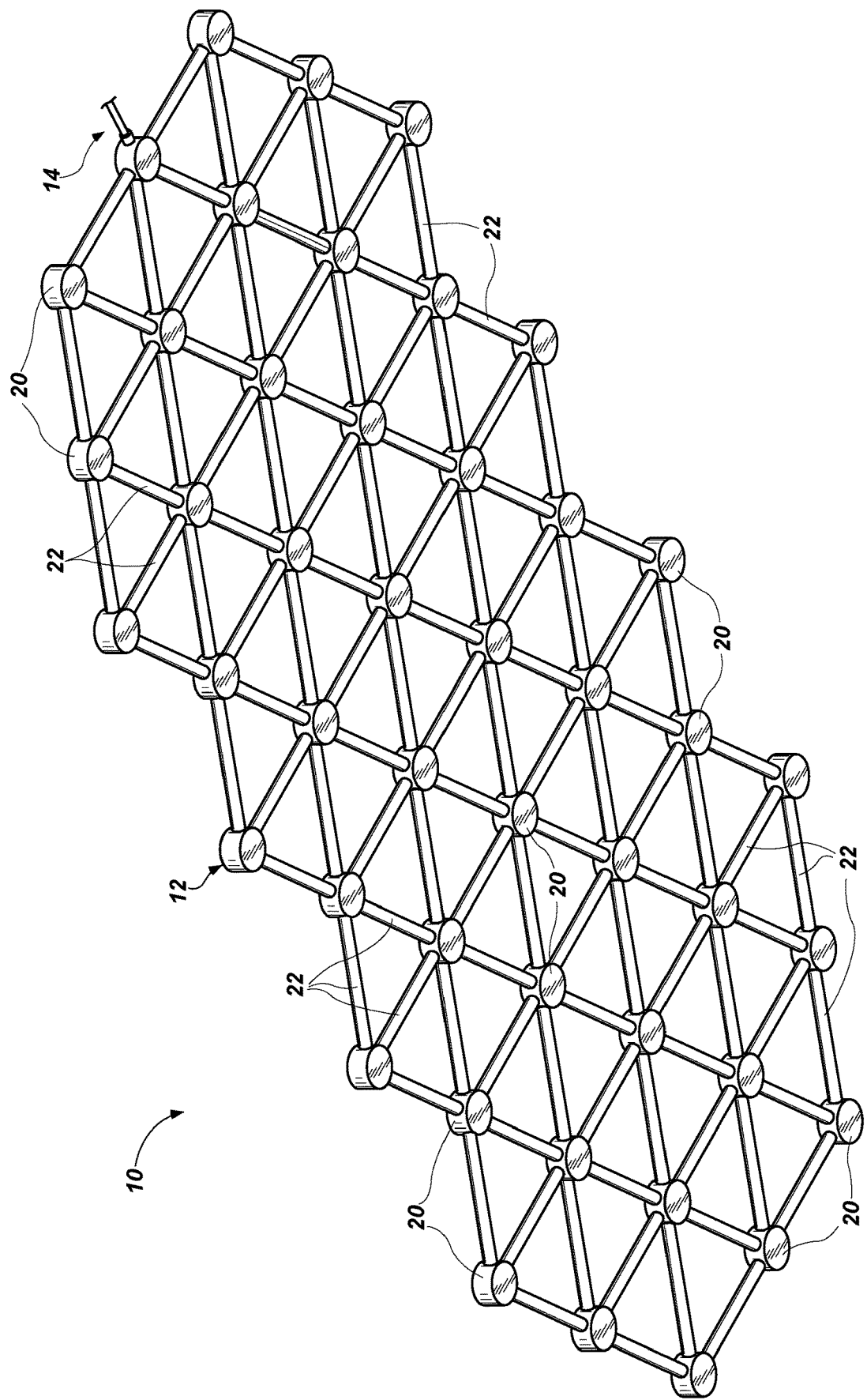
FIG. 10 is a bottom perspective view thereof.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, and to FIGS. 1 through 24 generally, a system 10 in accordance with the invention may typically include a web 12. The web 12 may be comprised of both mechanical components and electrical components. Typically, a power subsystem 14 or power system 14 will provide electrical energy to activate the web 12. Also, a cover system 16 (see FIGS. 22 through 24) as well as other padding, or the like may be used to render a user more comfortable, hide the web 12, or the like. Nevertheless, the web 12 may be used directly, and without any type of cover system 16 as seen in FIG. 1.

In general, a web 12 is formed of nodes 20. In the illustrated embodiments of FIGS. 1 through 17, the nodes 20 are comparatively short, right, circular cylinders appearing something like a puck 20. Individual nodes 20 are connected by connectors 22 or links 22, that operate as appendages, arms, legs 22 making both mechanical connections and electrical connections. As a practical matter, in certain presently contemplated embodiments, the nodes 20 and connectors 22, as to their mechanical component, may be molded from a resin simultaneously. As discussed hereinbelow, molding at ambient conditions, using a room-temperature-vulcanizing, silicone rubber is one suitable manufacturing process.

Meanwhile, the power subsystem 14 includes, among other components, a cord system 24. The cord system 24 may include a jack 26 or socket 26 in a node 20 of the web 12. A plug 28 or plug portion 28 may be inserted therein to effect electrical connection.

Referring to FIGS. 1 through 10, one will note that the web 12 is constituted by nodes 20, which may be in any suitable pattern. For example, the perimeter is typically hexagonal in the illustrated embodiments, with constituent triangles forming the overall matrix 12 or web 12. On the other hand, a rectangular arrangement is also possible. For example, the entire grid may be based on rectangles, rendering the overall perimeter rectangular. Accordingly, a Cartesian grid of nodes 20 interconnected by intermediate links 22 or legs 22 may contain the electrical components all electrically interconnected, dielectrically insulated, and mechanically protected by the nodes 20 and connectors 22.

Figure 11:
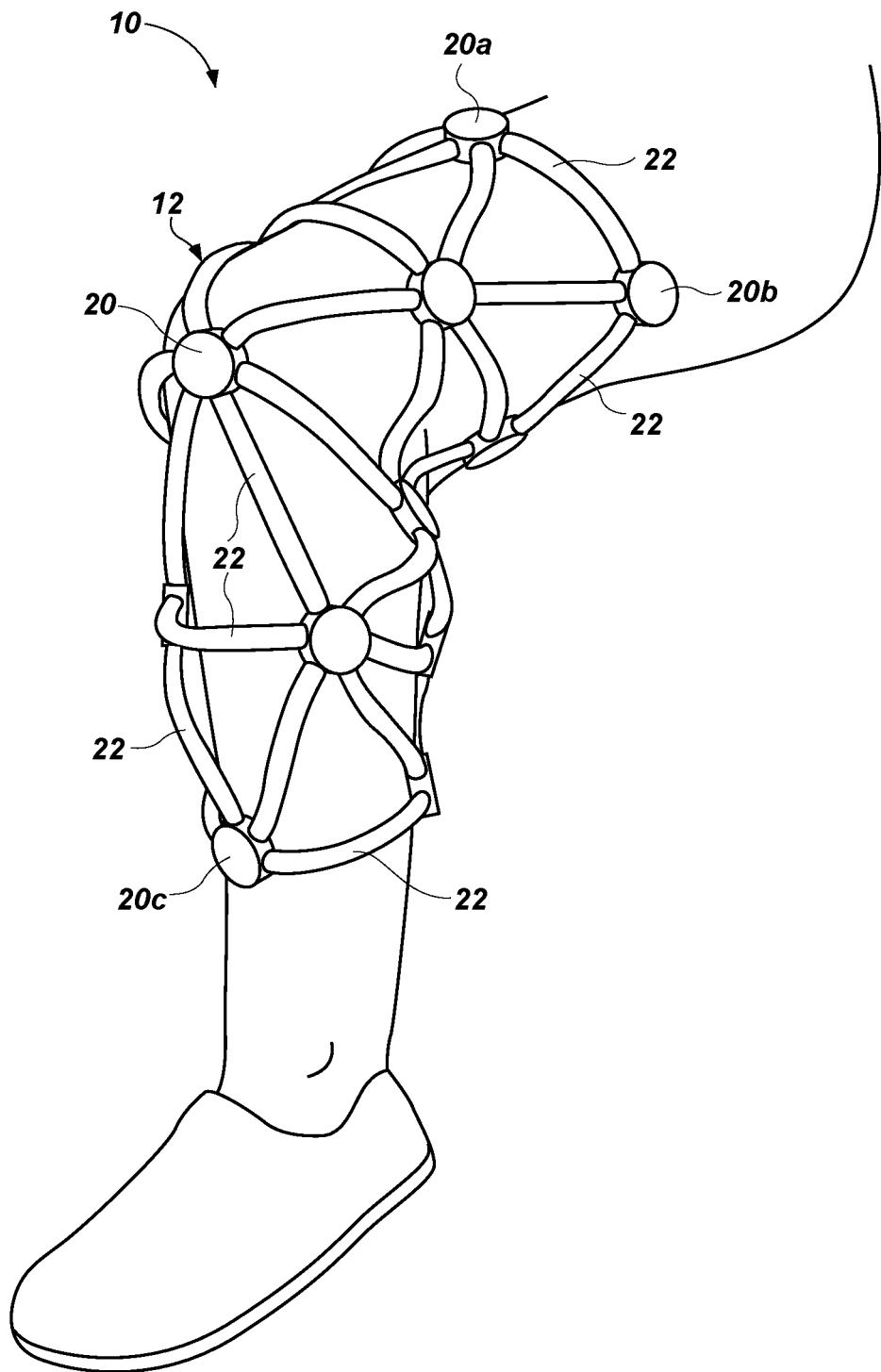
FIG. 11 is a perspective view of one embodiment of a PEMF web system, in accordance with the invention, wrapped around an appendage of a user.

Referring to FIG. 11, a web 12 in accordance with the invention may be wrapped around an appendage, such as a leg, arm, or head. Likewise, a particular area such as a knee, ankle, foot, shoulder, or the like may be wrapped with the web 12. Due to the mechanical connection of the nodes 20 by the links 22 or legs 22, all formed of an elastomeric resin, the web 12 may be highly flexible, without damage to intervening or contained electrical connectors. Thus, as illustrated in FIG. 11, the nodes 20 may be placed flat against the surface of the appendage in order to direct electromagnetic flux through the faces (e.g. flat faces) of the cylindrical nodes 20. One will note that the nodes 20a, 20b, 20c, in particular, actually are at approximately mutually orthogonal angles with respect to one another.

In this way, a region of a body or a bodily member may be bombarded by pulsed electromagnetic fields (sometimes referred to as electromagnetic forces) from several directions, and at varying intensities, based on the flux densities and the proximity of a node 20. Nevertheless, as illustrated in the upper leg portion of the web 12 of FIG. 11, several nodes 20 (for example, 20a, 20b, and others) are directing pulsed fields electromagnetic from different angles into the same region of space within the appendage.

Likewise, one will note that the various runners 22, legs 22, or connectors 22 are in various states of distortion. For example, on the one hand, certain of the connectors 22 wrap conformally around the appendage, effectively using the entire length of the connector 22. Other connectors 22 are bent, buckled, folded, and the like, in order to effect the position and wrapping of the web 12 about the appendage.

Because of the lack of intervening material (mechanical uncoupling in two dimensions), of either electrical connection, mechanical connection, or both, the web 12, in accordance with the invention, is well adapted to conformal shaping around the user. In contrast to prior art devices, such as chairs, mats, and the like, having mechanical structure incapable of such arbitrary, conformal shaping, are considerably more limited.

Moreover, due to the solid core construction of the nodes 20, as discussed hereinbelow, flux intensities are greater, penetration distances are greater, and immersion is much more complete. Also, the multiplicity of the nodes 20 as well as their compactness and intensity provide substantially more directed, more intense, if desired, and more penetrating, pulsed, electromagnetic forces.

Figure 12:
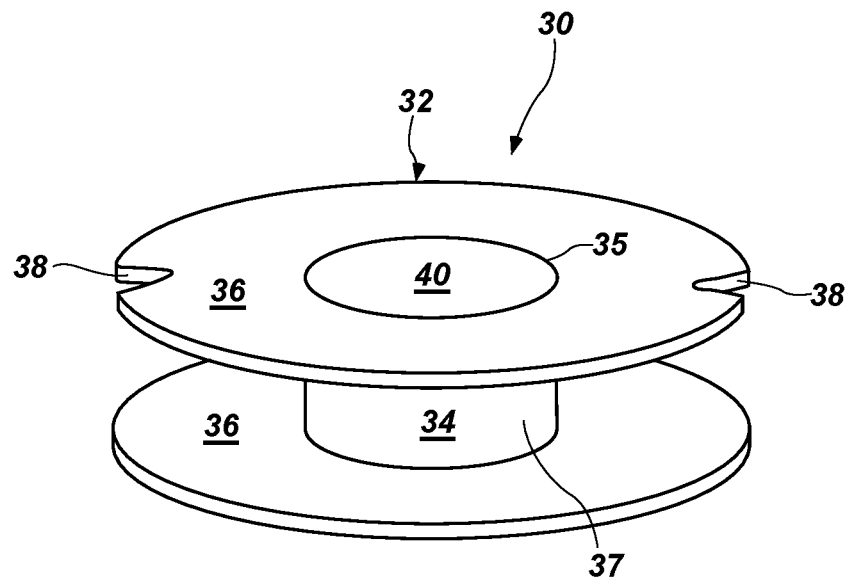
FIG. 12 is a perspective view of one embodiment of a spool and core for receiving wire turns to form a micro-coil electromagnet.
Figure 13:
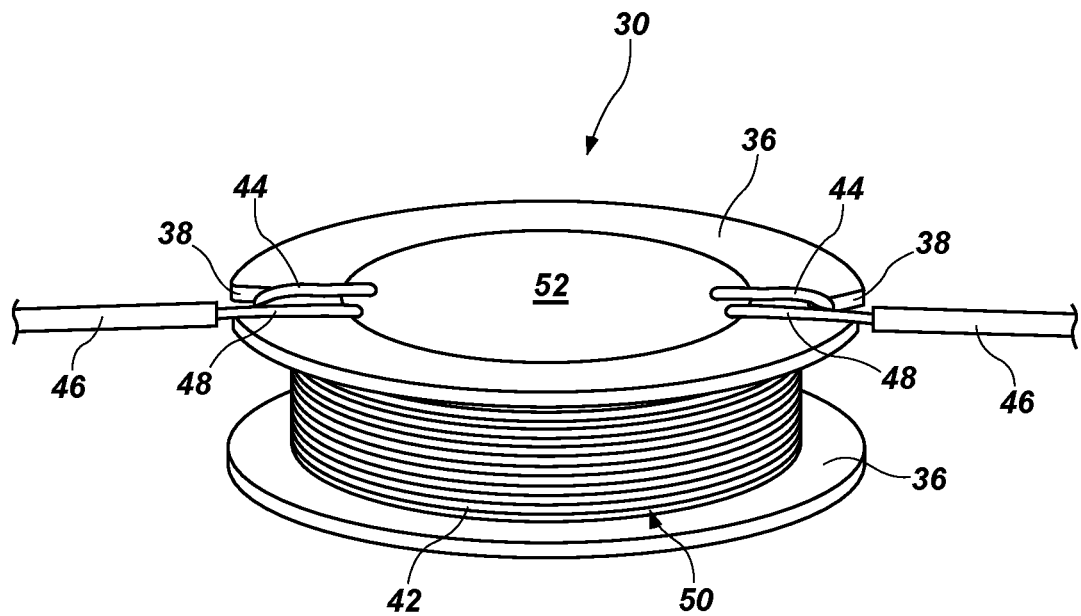
FIG. 13 is a perspective view of one embodiment of a completed micro-coil.
Figure 14:
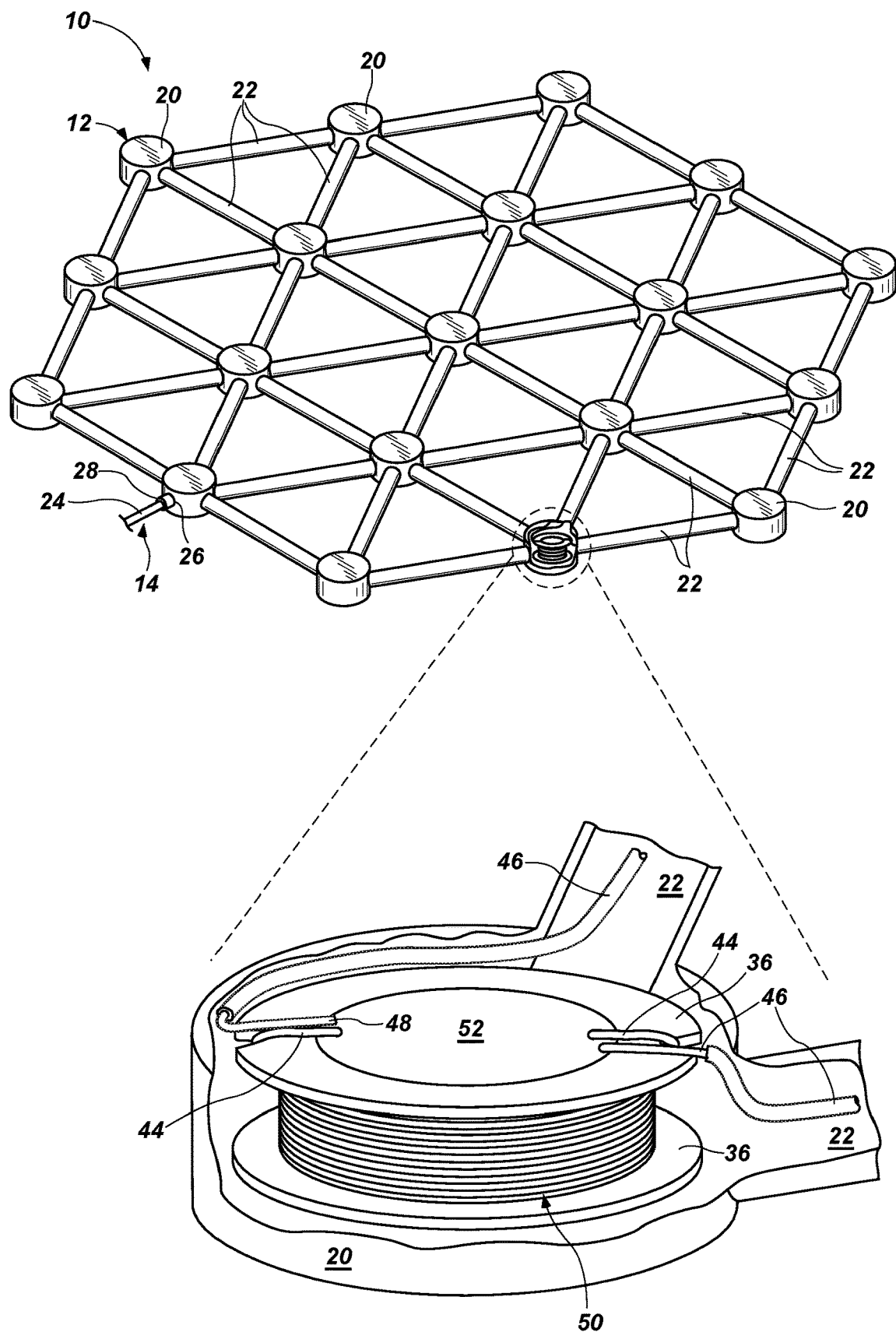
FIG. 14 is a partially-cut-away, detailed, perspective view of the embedment of a micro-coil within a node of one embodiment of a PEMF web in accordance with the invention.

Referring to FIGS. 12 through 14, each of the nodes 20 may form a source 30 of pulsed electromagnetic fields and corresponding force. U.S. Pat. No. 8,439,816 is incorporated herein by reference, and describes in detail various mechanisms for manufacturing, assembling, and using electromagnetic sources 30.

In the illustrated embodiment, each of the nodes 20 may include a spool 32 embedded therein. Prior to being embedded in the resin, such as the RTV silicone resin mentioned hereinabove, the spool 32 may have wrapped around its barrel 34 or drum 34 an electrical conductor to form an electromagnet. Meanwhile, the inside aperture 35; the drum 34 of the spool 32 may hold an iron core for such a magnet. A flange 36 on each end of the drum 34 provides containment of wire turns.

In the illustrated embodiment, wraps or turns of wire may be laid around the outer surface 27 of the barrel 34, and be contained on each end thereof by the flanges 36. Upon achieving the proper number of turns, wire may be passed through an aperture 38 or notch 38 that operates as a holder 38 to maintain tension and stability of the turns on the spool 32.

A core 40 formed of suitable iron may fit within the aperture 35 through the drum 34. This core 40 operates as a flux director 40 or a flux guide 40. It concentrates flux lines preferentially, compared to air or other media.

For example, electromagnetic flux lines passing through a coil of wire immediately begin to repel one another, and typically wrap back out and around the coil that generated them. Thus, with distance, and particularly along a center line normal to such a coil (e.g., along the central axis running perpendicularly through such a coil), magnetic flux attenuates rapidly and disperses radially away therefrom.

In contrast, an iron core 40 attracts, collects, and concentrates all flux lines through it and provides them direction and intensity normal to the face (end face) of the spool 32 and core 40. Thus, flux density is increased, penetration distance is increased, magnetic and the field from the source 30 is generally more intense, localized, and effective.

Typically, the drum 34 is wrapped with wire 42, which will act as magnet wire 42. In the illustrated embodiment, it has been found suitable to provide from about 20 to about 200 turns with a target of about 93 turns of wire 42 on each spool 32. The spools 32 are approximately 2 to 3 centimeters in diameter across the flanges 36. Meanwhile, the drum 34 is less than a centimeter long, and typically closer to half a centimeter long. Thus, wire gauges on the order of 40 have been found suitable for wrapping around the spools 32.

At each end 44, the wire 42 is stripped of insulation. Typically, the wire 42 will be coated with a specific, flexible, insulating coating that acts like a dielectric varnish or shellac. Thus, this insulating coating may be stripped from a portion of each end 44 in order to render each spool 32 a separate unit. This has been found more suitable than a process of making all the spools 32 interconnected by the magnet wire 42, itself running between spools 32.

Instead, the ends 44 are bonded to wires 46 formed in comparatively shorter lengths embedded within each of the connectors 22 of the web 12 and matching the lengths thereof. For example, each of the ends 48 of each segment 46 or leg of wire 46 will typically be stripped of insulation. In the illustrated embodiment, the wires 46 are coated with a standard plastic insulated coating. That insulated coating may be stripped from the wire 46 along a suitable distance in order to expose the bare ends 48.

Accordingly, the ends 44, 48 may be soldered together. As noted above, the notches 38, acting as holders 38, may each receive an end 44 of the magnet wire 42. Typically, these ends 44 may simply be drawn from the coil 50, wrapped around the drum 34 of the spool 32, and wedged into the appropriate notch 38. Thereafter, the end 44 may be bent flat against the flange 36 in preparation for soldering to the end 48 of the respective wire 46 that will interconnect that particular node 20 to its adjacent nodes 20.

Inasmuch as each node 20 may easily be connected in series in the currently contemplated embodiment illustrated, each coil 50 need only connect to two connecting wires 46. In other embodiments, also possible, multiple wires 46 may pass along the connectors 22. Thus, it is possible to make a parallel connection or even independent operation of each coil 50. However, in the illustrated embodiment, it has been found completely suitable to connect each of the coils 50 of an entire web 12 in series. Thus, all of the coils 50 with their cores 40 are activated at once according to the programmed activation. Again, reference to the documents incorporated herein by reference will provide various ranges of power, duty cycles, and so forth.

One will note that a cover 52 operates as an insulating plate 52 to prevent electrical contact between any of the ends 44, 48 and the iron core 40. In one presently contemplated embodiment, the cover plate 52 may simply be a paper or plastic layer provided with a suitable adhesive on one side. Thus, the cover 52 adheres to a flange 36 having the notches 38. In certain embodiments, both flanges 36 on each spool 32 may be provided with a pair of notches 38. Thus, there is no orientation requirement for the spool 32. That is, the spools 32 may be laid with either flange 36 up, and still receive the ends 44 of the magnet wire 42.

The cover 52, having a suitable adhesive may also provide a temporary connector to secure the core 40 inside the drum 34. The cover 52 prevents the drum 34 from passing beyond the cover 52, and the adhesive on the cover 52 provides adhesion to keep the core 40 lodged against the cover 52. Eventually, the casting of the web 12 embedding the spools 32 with their wires 42 and connectors 46 in the nodes 20 and connectors 22 of the web 12 will render unnecessary the adhesive nature of the cover 52. However, the insulating nature of the cover 52 is still important.

Referring to FIG. 14, a cut-away view of a coil 50 wrapped about a spool 32 inside a node 20 demonstrates one reason for the sizing of the nodes 20. However, another purpose in sizing the nodes 20, in addition to containing and covering the spools 32 and coils 50 with their connections to the wires 42, 46 is to provide the proper aspect ratio between the height and diameter of each of the cylindrical nodes 20. Thus, each of the "pucks" 20 becomes a medallion 20 that may be placed flat against the surface of a treated member. Also, the aspect ratio of height to diameter provides stability in such situations or when used in a mat, bedding, or the like.

Figure 15:
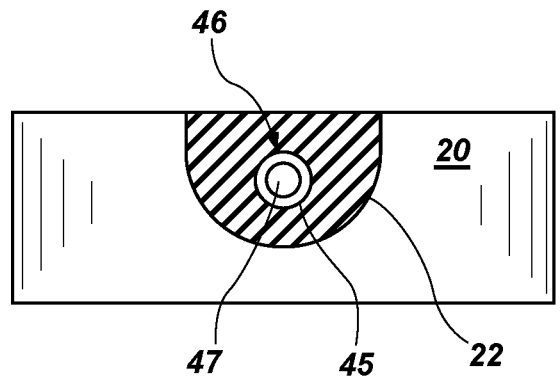
FIG. 15 is an end, elevation, cross-sectional view of one embodiment of a connector connected to a node, and embedding a wire there within.

Referring to FIG. 15, one may see the wire 46 with its central conductor 47 covered by an insulating layer 45. In general, the connector 22 is substantially larger than the wire 46. Thus, the connector 22 or the resin of the connector 22 that becomes a flexible, preferably elastomeric, polymeric jacket 22 provides a substantial radius any time the connector 22 is bent along its length. Thus, the wire 46 does not undergo significant risk of damage.

For example, if the conductor 47 were solid, then the wire 46 might break after several cycles of bending. However, if the conductor 47 is stranded, the more finely the better, as a bundle of comparatively thin strands together, then the wire 46 becomes much more flexible. It undergoes much less strain (i.e. engineering definition), and so can undertake numerous, hundreds, or even thousands of cycles of bending, without undue distortion, yielding, hardening, or breakage.

Figure 16:
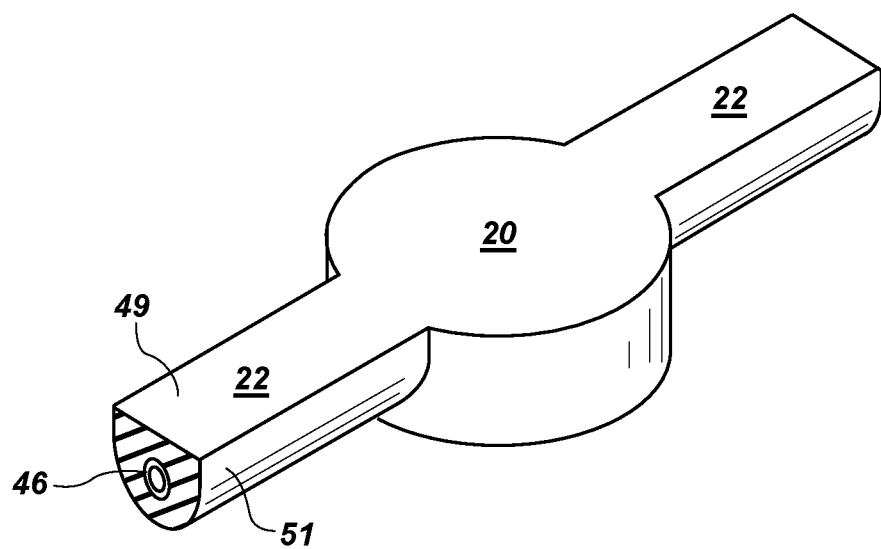
FIG. 16 is a perspective view thereof, representing a segment of a web.

Referring to FIG. 16, in one presently contemplated embodiment, the legs 22 or connectors 22 between nodes 20 have a flat upper surface 49. This stands in contradistinction to the curved lower surface 51. It has been found that molding is much more effective, rapid, and aesthetically pleasing if bubbles and other sources of inclusions are eliminated.

Thus, as will be described hereinbelow, a poured web 12 has been found suitable and results in the flat upper surface 49 in one presently contemplated process. That is, for example, by leaving the mold open, so that air bubbles and the like may freely exit the uncured resin, a better quality web 12 may be cast. Thus, it has been found preferable to pour into an open mold, rather than relying on closed mold technologies.

Figure 17:
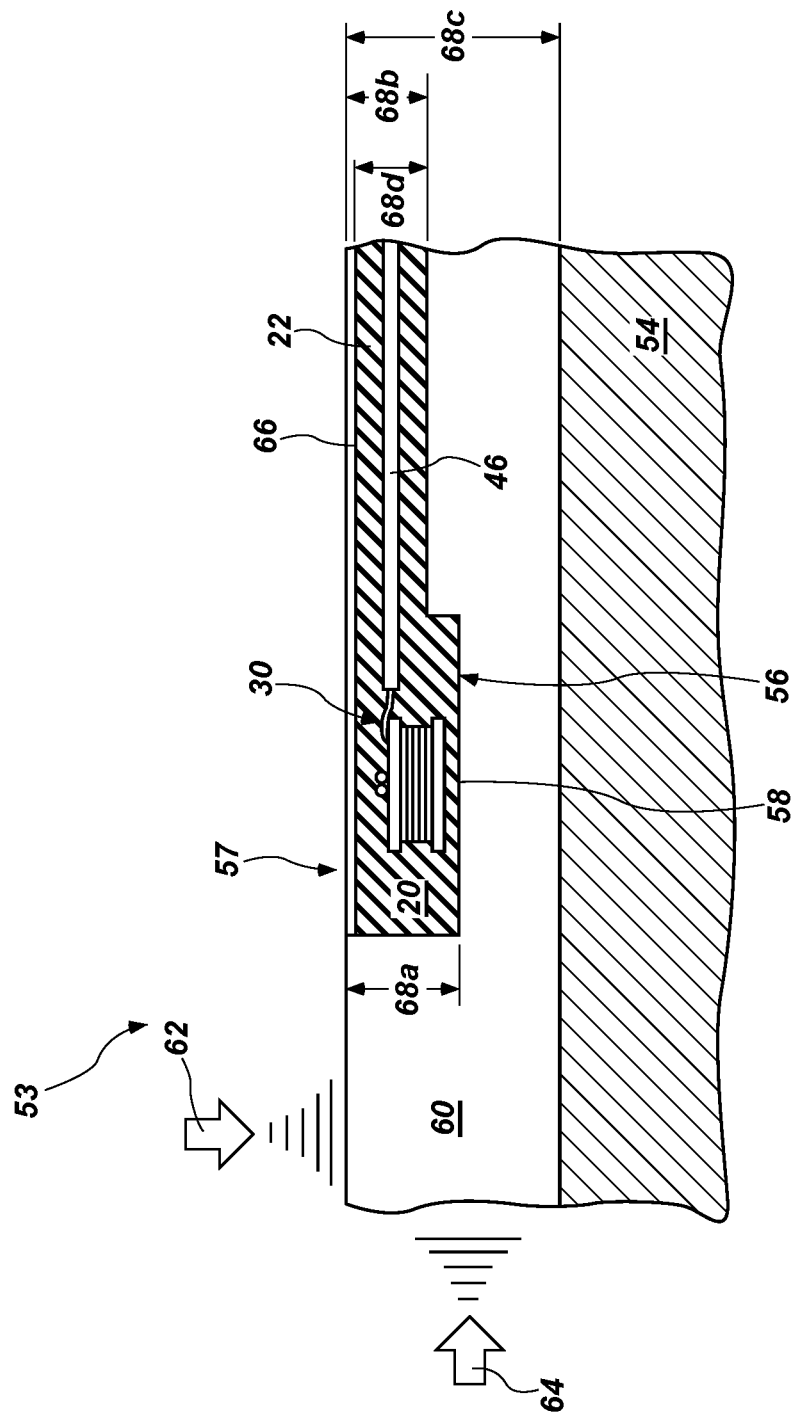
FIG. 17 is a cross-sectional view of a portion of one embodiment of a mold for cold molding a web in accordance with the invention.

Referring to FIG. 17, in certain embodiments of apparatus and methods for fabricating the system 10 in accordance with the invention, a process 53 may include mounting on a substrate 57 a system forming a cavity 56 having an open top 57 and a floor 58. The open top 57 is responsible for receiving the material that will fill the cavity 56 of the mold 60. Likewise, the open top 57 is responsible to evacuate or carry away any bubbles, outgassing, and the like that may result from the molding process 53.

In the illustrated embodiment, the substrate 54 or base 54 supporting the mold 60 may be fixed or movable. In certain embodiments, the base 54 or substrate 54 may actually be a table equipped to vibrate, shake, move, or otherwise provide vertical actuation 62, horizontal actuation 64, or both.

For example, vibrating will typically shift heavier materials downward in the presence of lighter materials. This means bubbles of gas will typically shift higher while molecules of resin shift lower in the cavity 56 of the mold 60. Settling occurs for multiple reasons, but actuation 62, 64 assists by causing momentum transfers resulting in movement, promoting rising of gas bubbles or air bubbles from entrapment through the molded product 20, 20 into the surrounding air.

The upper surface 66 of the poured resin filling the cavity 56 of the mold 60 will typically be approximately flat. Some shrinkage or the like may cause a shape other than an exactly flat top surface 66 or upper surface 66. However, as a practical matter, it has been found an improved process 53 to leave the open top 57, allowing gases to escape. This provides a better result than does injection or other introduction of the resin into the cavity 56 with simultaneous or subsequent extraction of gas in the cavity 56.

Thus, in the illustrated embodiment, the floor 58 of the cavity 56 may be machined out, molded, or otherwise formed to have various depths 68a, 68b. For example, the wire 46 needs comparatively little depth 68b. It merely needs sufficient distance 68d between the upper surface 66, and the floor 58 under the connector 22.

In contrast, the depth 68a for the node 20 requires accommodation of an entire spool 32 with its coil 50 and the connections of the ends 44, 48 of the respective wires 42, 46. Typically, the upper surface 66 will be at the same level for both the nodes 20 and the connectors 22 or runners 22 therebetween. In contrast, the particular level of the floor 58 may vary according to the designs of various components 20, 22.

Ultimately, the full depth 68c of the mold 60 will include additional material to provide a thicker wall for purposes of mechanical strength, cooling, possibly, in cases of hot materials, or the like. However, in certain embodiments, the mold 60 need not tolerate a significant amount of heat either for cure or for the heat of reaction of a resin forming the nodes 20 and runners 22.

Rather, certain polymers, such as polyethylene, polypropylene, or the like may be suitable. Thus, not needing the mass of steel, the wear resistance of steel, nor the high heat transfer capability of aluminum, an operator of the process 53 may use various modest temperature (close to ambient conditions) and pressures (virtually no difference from the bias of ambient pressure) in order to cast or otherwise mold the webs 12.

Figure 18:
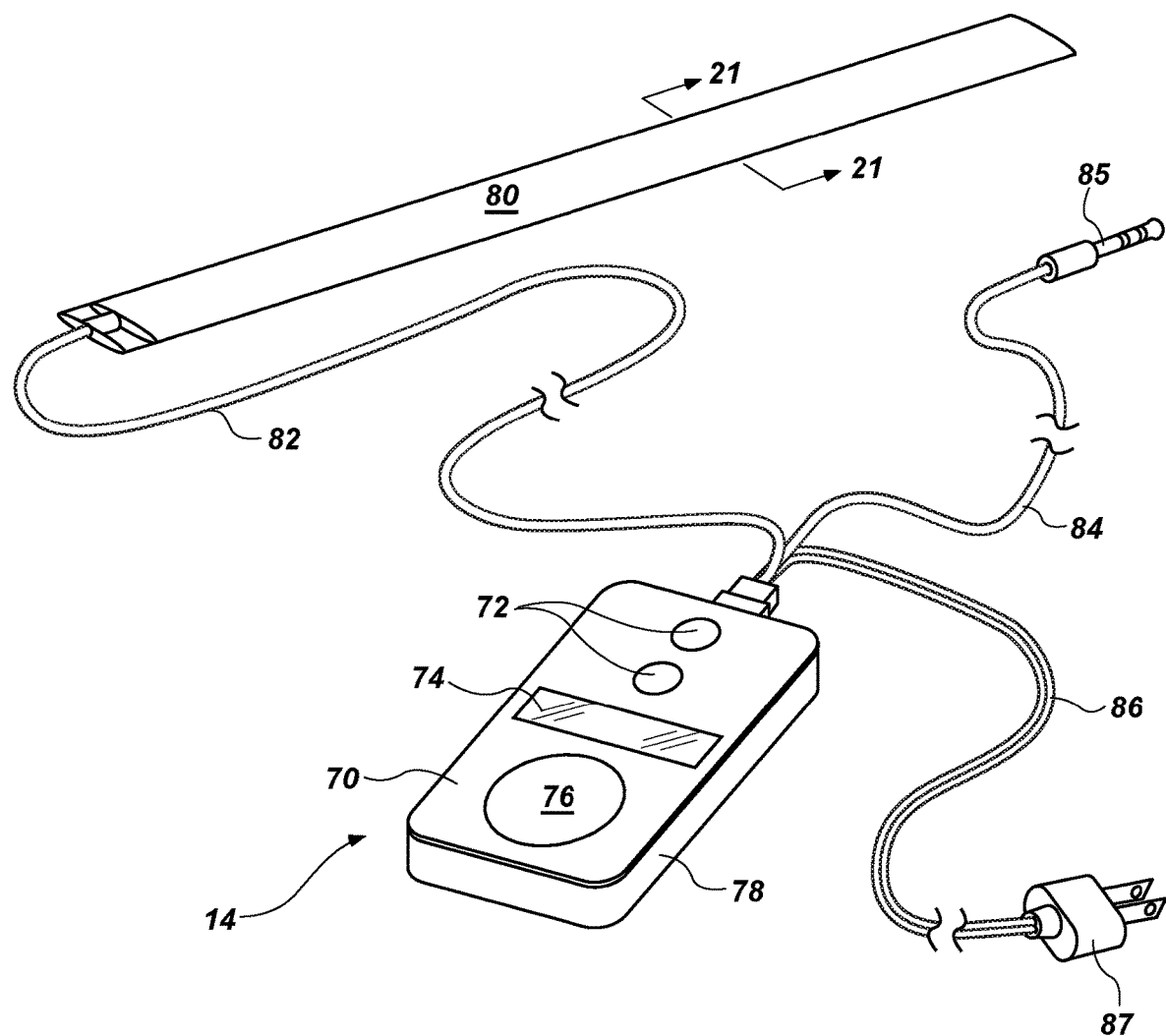
FIG. 18 is a perspective view of one embodiment of a controller with various connectors, lines, and switches in accordance with the invention.

Referring to FIG. 18, in one embodiment of an apparatus and method in accordance with the invention, a controller 70 may include tactile buttons 72 for interaction with a user. Whether the buttons 72 constitute an entire keyboard, a plurality of buttons 72, or a single button 72, some interaction with a user will typically be required. Accordingly, the controller 70 may be provided with computerized access, keyboard access, flash drive access, or the like.

However, in the illustrated embodiment, buttons 72 serve to actuate the processes of the controller 70. A microprocessor, computer, or the like may be embedded within the controller 70, resulting in inputs from a user by way of the buttons 72, by another computer, or both. Any output or visible information may be presented in a window 74 or a display 74. Other features 76 may include meters, read-outs, displays, logos, instructions, warnings, or the like.

Typically, within a housing 78 of a controller 70 will be contained electrical power equipment. It may power the electronic functions of the controller 70 as well as logic, a circuit board, micro processor chips, or the like. Microprocessor-based controllers 70 are known in the art and have been described in literature incorporated herein by reference.

Various mechanisms may constitute a switch 80. It has been found suitable to use a snap switch that may also be referred to as a distributed switch 80, ribbon switch 80, or tape switch 80. This will be described hereinbelow in somewhat more detail. Meanwhile, a cable 82, constituting an electrical conductor 82 may pass from the controller 70 to the switch 80 providing for automatic on and off functionality for the system 10, in the presence or absence of a subject (e.g., pet, person, etc.) lying on the switch 80. Meanwhile, another cable 84 may be provided with a plug 85 that makes an electrical connection with the circuit within the web 12.

Likewise, wall power (power from an electrical outlet) may be received by the controller 70 for distribution to the switch 80 and to the web 12 through the line 84. Accordingly, a line 86 or electrical cord 86, may be constituted by a common cable 86 carrying conductors from a plug 87 connected to standard wall current. In operation, the controller 76 may receive all power from the line 86, and may include power supplies, power management circuitry, and the like as known in the art. Accordingly, power from the line 86 powers the controllers 70, as well as the web 12 by way of the line 84 and plug 85.

The switch 80 is a somewhat different matter in that the switch 80 consumes only trivial amounts of power, and only as losses. The functioning of the switch 80 is simply to determine occurrences of a displacement, distortion, deflection, or the like of the switch 80. Deflection indicates the presence of the user. A resulting "snap" bend thereby closes the switch 80 or triggers the switch 80 to make a closed circuit which is indicated to the controller 70.

In some embodiments, the switch 80 may actually carry the power that eventually is passed by the line 84 to the web 12. In other embodiments, the switch 80 simply needs to provide a closed circuit, which may be detected by a voltage, current flow, or the like by some element within the controller 70. Thus, the switch 80 need not carry any significant "power" on the order of actual power usage through the line 84 by the web 12. The switch 80 may be in the circuit of the line 84, or may not be. However, in currently contemplated embodiments, the voltage across the plug 87, and thus carried by the line 86 is that of wall power. Accordingly, a power supply embedded within the controller 70 modifies and manages the power, voltage, and current in order to provide a comparatively low voltage, on the order of single digits or tens of volts.

Typically, voltages above about 15 to 20 volts would be uncommon. This is in contrast to the 110 to 120 volts of wall power. Similarly, the switch 80 may be a comparatively low voltage (on the order of 5 to 15 volts, typical of electronics, and only milliamps of current or less.

Referring to FIG. 19, while referring generally to FIGS. 19 through 21, and more generally to FIGS. 1 through 24, in certain embodiments, a switch 80 may be embedded within a cover 88 or housing 88. The housing 88 or cover 88 may be formed of plastic, bonded plastic components, or an extruded plastic tube. It may be a fabric sleeve, a sleeve formed of multiple pieces of fabric bonded together, sewn together, or otherwise connected. It may be a simple piece of fabric wrapped and sewn into a tubular cross-section suitable to enclose the operating components of the switch 80.

In the illustrated embodiments of FIGS. 19 through 21, a cover encloses a first conductor 90 and a second conductor 92. Between these two conductors 90, 92 is placed periodically an insulator 94. The insulator 94 will typically be configured in segments. The insulator 94 or spacer 94 maintains apart the conductor 90 from the conductor 92. Together, contact between the conductors 90, 92 will pass electrical current, however large or small. It will show a closed circuit, rather than an open circuit otherwise maintained by the spacer 94 or insulator 94.

Typically, the insulator 94 is formed of a dielectric material, such as plastic, a tape, or the like. In certain embodiments, the insulator 94 may simply be a dielectric tape manufactured to match or exceed the width of each of the conductors 90, 92. It may be cut into segments that provide anywhere from about 20 to about 80 percent open space between the conductors 90, 92.

For example, in one currently contemplated embodiment, a width of about 13 millimeters for the conductors 90, 92 has been found suitable, with a spacer 94 acting as an insulator 94 of the same width. However, it has been found that making the insulator 94 in small squares, one may place the segments 94 at a distance of several lengths apart. Thus, the bending of the switch 80 results in a ready contact between the conductors 90, 92 at some point along the length thereof intermediate adjacent insulators 94.

As a mechanical operation, the switch 80 may include the conductors 90, 92 formed of copper, or formed of a copper-coated metal, such as steel. Thus, the conductors 90, 92 may actually operate as springs, and specifically as "tape" springs that have a tendency to maintain a curvature, operating very much like the blade of a tape measure.

In the illustrated embodiment, in order to make the electrical contacts between the conductors 90, 92, the conductors 90, 92 and the spacers 94 need to all be formed to be concave in the same direction. Thus, another equilibrator 96 may be formed and positioned to operate in an opposite direction.

For example, in the illustrated cross-sectional views (FIG. 19 having an exploded view as well as the end, cross-sectional view thereof), the stackup of components 88, 90, 92, 94, 96 is illustrated. Each of the conductors 90, 92, as well as the equilibrator 96, will preferentially kink (in bending along their length as a beam) in one direction over the other. The equilibrator 96 provides a counteracting force, tending to return to, and keep the conductors 90, 92 and the equilibrator 96 in, an equilibrium position, which is straight with only the natural curvature across the width.

In contrast, pressure applied at some point along the beam 80 that is the switch 80 will cause distortion, flattening out the curvature illustrated. Eventually, a pronounced bend or kink is caused by the elasticity and deflection of those elements 90, 92, 94, 96. The equilibrator 96 provides sufficient force that will bias the switch 80 back to an open position and a straight position.

Referring to FIGS. 19 through 21, the embodiment of FIG. 19 shows a cover 88 formed of two pieces having some fastener 98 or fastening 98 extending lengthwise therealong. This may be a heat seal, a seam, a weld, a glue line, or the like. Thus, according to the material from which the cover 88 is made, a particular fastener 98 or fastening mechanism 98 may be employed.

In contrast, the embodiment of FIG. 20 involves a single wrap of material that is then bonded 98 or fastened 98 at the extremity 99 or edges 99 only where they join. Since the cover 88 constitutes a wrap around the internal components 90, 92, 94, 96, only one line long the length of the switch 80 is required to be closed.

Referring to FIG. 21, it has been found advisable to maintain sufficient space within the housing 88 or cover 88 to permit free motion by the conductors 90, 92 and the equilibrator 96. Thus, in the embodiment of FIG. 21, the housing 88 may be formed of a material such as an extruded plastic, rubber, a woven continuous sleeve 88, or the like. However, it has also been found that heat-shrunk tubing does not serve well for the cover 88. Part of the "heat shrink" function is to bind bundles of wires or cables together by applying compression, corresponding to tension within the tubing itself. That tension applies forces that distort, deflect, or override the bias forces within the conductors 90, 92 and the equilibrator 96 in the neutral position. Accordingly, it has been found that interference by the housing 88 or cover 88 is problematic. Some slack must be accommodated.

Figure 22:
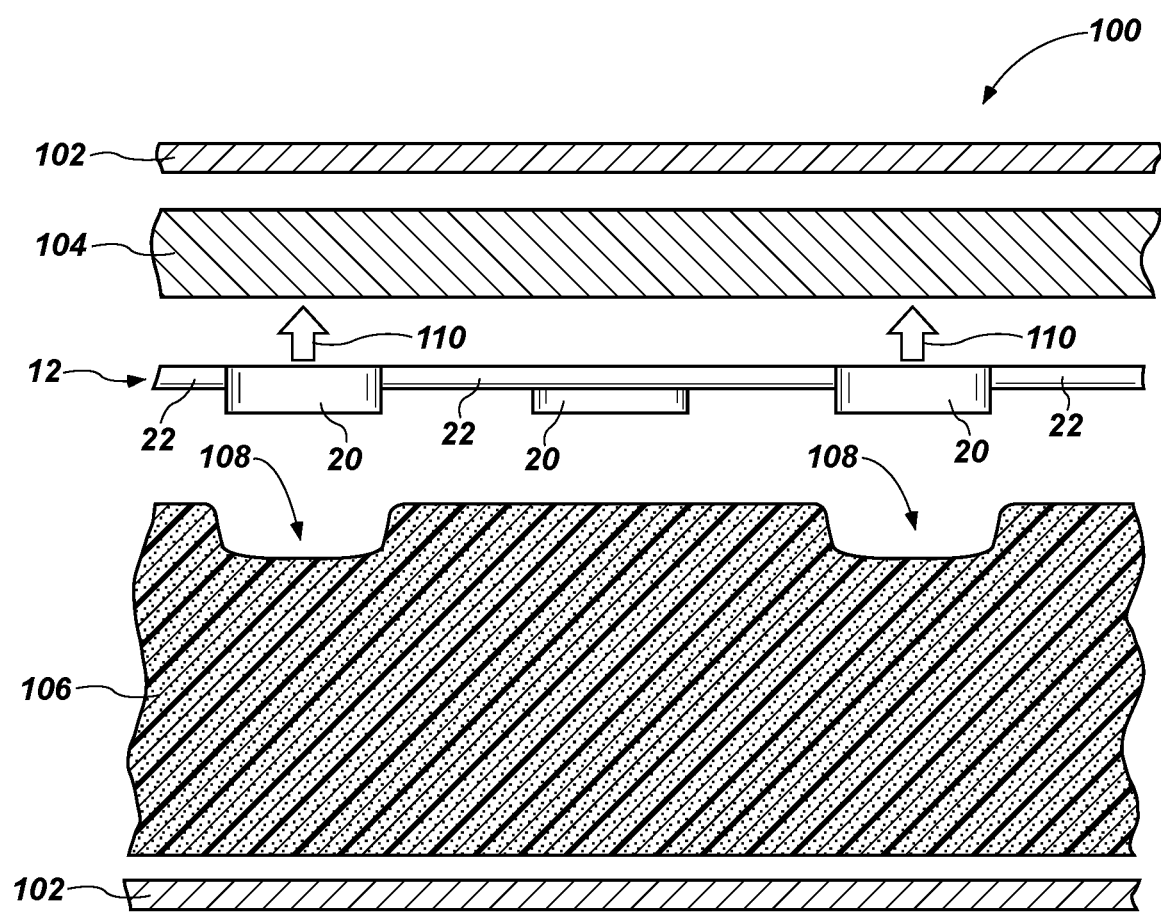
FIG. 22 is a cut away, cross-sectional, exploded view of a portion of a bedding system having a web in accordance with the invention incorporated there within.

Referring to FIG. 22, a web 12 may be embodied as part of a pet bed 100, or the like. In the illustrated embodiment, a portion of a cross-section of one embodiment of such a pet bed 100 has a cover 102 that may circumnavigate the entire structure 100. Typically, a layer 104 of foam, batting, or the like, such as a flexible elastomeric foam, or the like may be used to conform to the comparatively flexible cover 102.

A web 12 may be embedded in the bulk padding 106 in the bed 100. Many pet beds 100 are formed with a padding 106 constituted by shredded urethane or other elastomeric foam. This elastomeric foam in pieces readily forms recesses 108 to accommodate the web 12 embedded therein. In other embodiments, the web 12 may be accommodated by recesses 108 actually formed in a monolithic or otherwise molded foam pad 106. It has been found that chopped foam as the bulk padding 106 seems to work well, and accommodates readily the increased stress caused locally within the padding 106 by the presence of the nodes 20, runners 22 or connectors 22, and so forth. Thus, it has not been found necessary to pre-form the recesses 108. Instead, those recesses 108 are naturally formed by the weight of a body on the top of the cover 102. The direction 110 of the electromagnetic flux lines propagated through the cores 40 by the coils 50 in each of the nodes 20 passes directly across a comparatively short distance required to reach a user. Meanwhile, forces opposite the direction 110 of weight will tend to press the web 12 into the mat 106 or padding 106.

Figure 23:
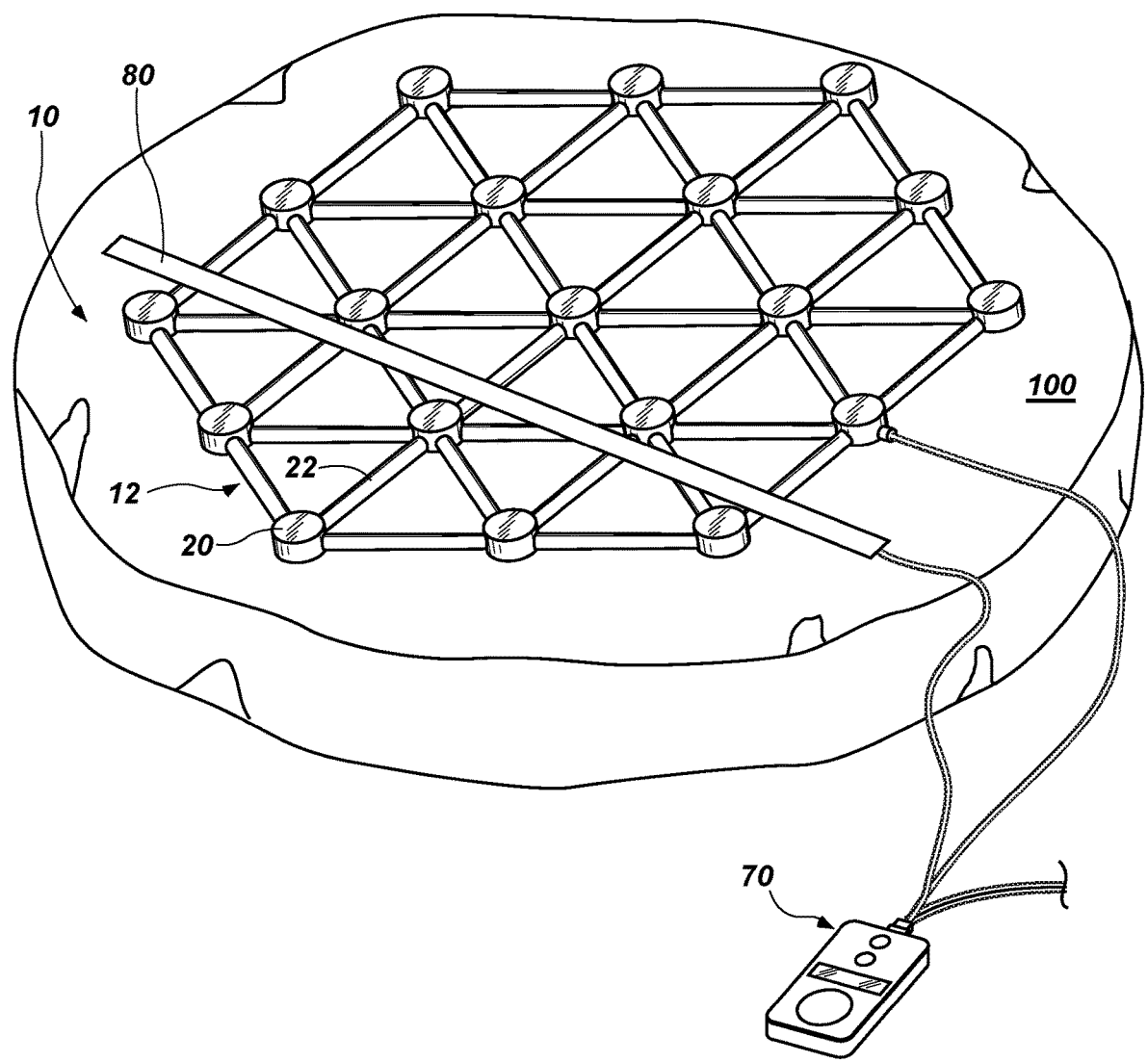
FIG. 23 is a perspective view of several components of a web PEMF system in accordance with the invention lying on a pet bed into which they may be embedded, thus showing their comparative sizes and configurations.

Referring to FIG. 23, a system 10 is illustrated having a pet bed 100 into which is embedded a web 12 such as that shown (for comparison) on top of the bed 100. In certain embodiments, the web 12 and the overall system 10 may actually be placed under a blanket on top of a pet bed 100. However, it has been found suitable to build the web 12 into the pet bed 100, and particularly inside the cover 102 in order to provide additional comfort. Meanwhile, the switch 80 over the web 12 detects deflection caused by the weight of a body resting thereon. This activates the switch 80, closing its circuit, and notifying the controller 70 to operate the pulsed electromagnetic field according to a pre-programmed regimen.

Figure 24:
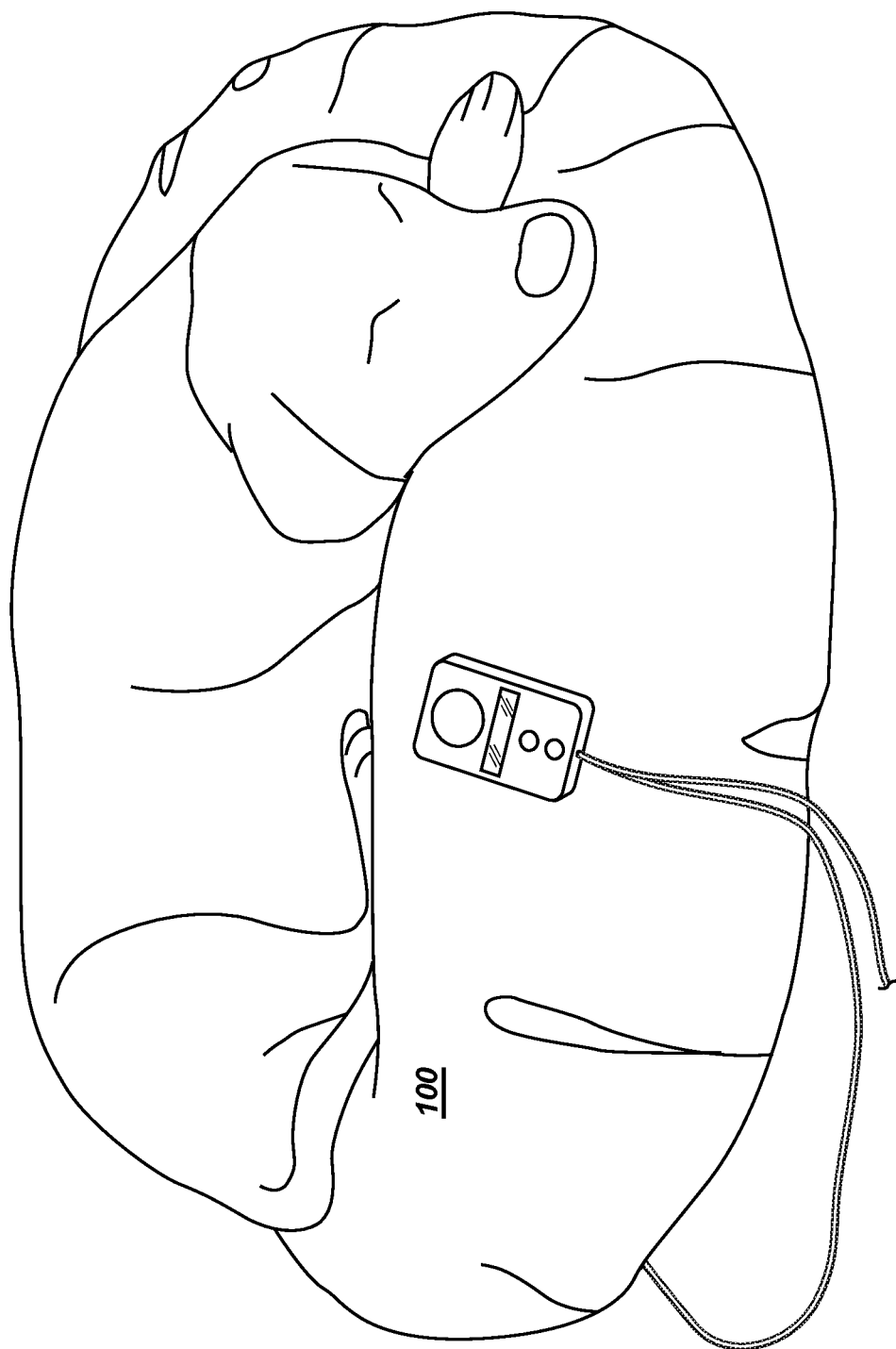
FIG. 24 is a perspective view of a pet on the pet bed of FIG. 21, having the web system embedded there within.

Referring to FIG. 24, while continuing to refer generally to FIGS. 1 through 24, a pet using a pet bed 100 need not be aware of the web 12 with its electromagnetic pulse system. The pulse is assisting with cell regeneration of both soft and hard tissues, as well as other healthy conditions.

One will note that prior art attempts at using electromagnetic force or pulsed electromagnetic field (PEMF) have focused on large loops, mats that appear like old fashioned braided rag rugs in which a large oval is formed by sewing together thick cords of braided fabric material. As a practical matter, such systems often necessarily required stabilization or support by chairs, tables, other large structures, and so forth. Each of such systems relied on several loops arranged in a large flat more-or-less planar "rug" of loops.

In contrast, a system and method in accordance with the invention produce substantial benefits in a focused approach. They also employ a more narrowly focused and directed PEMF generator 30 or source 30. For example, micro-coils 50 in accordance with the invention have a diameter less than 2 inches, and may often have a diameter less than an inch. Moreover, their thickness may be less than a centimeter, and may be half a centimeter or less. Likewise, rather than applying a PEMF pulse over a long period of time, duty cycles may be on the order of about 10 percent.

In experiments it has been found that a PEMF treatment lasting more than a total of two hours per day of actual application of pulses is sufficient to meet the maximum benefit. Continued exposure over a cumulative time greater than two hours has not proven effective. Instead, two modes may be used for applying the suitable duty cycle or total exposure time.

First, a duty cycle that turns the controller 70 on or provides through the controller 70 a series of pulsed PEMF wave forms may have a duty cycle of from about one to about one hundred percent. Typically, during a day, the controller 70 may be programmed to provide pulses over a time period that represents a specific fraction of the time that a user will spend exposed to the web 12.

For example, if a user is sitting in an arm chair or other comfortable seating, for example, watching a movie or the like at home, then the user may desire to have the entire treatment completed within one two-hour block of time. Accordingly, the duty cycle of the controller 70 may be set for one hundred percent. Timers may be set to control the pulses to occur or present a treatment over a total of two hours at one hundred percent duty cycle. Such treatments are favored by active people who have specific treatment needs.

On the other hand, if a subject is to be exposed to the web 12 as part of bedding, such as in the pet bed 100, or in a mat suitable for human use, then one may set the duty cycle to accumulate a total of two hours of exposure during the entire time of use. A user may have a twenty percent duty cycle operating throughout an eight hour night of sleep. This provides the maximum effective dosage of two hours total during a period of the eight hours of sleeping.

Likewise, a pet or human user may rely on a pre-programmed regimen controlled by the controller 70 and timing the use over a twenty four hour day. In such an event, the switch 80 may be used to detect the presence of a user, such as a person or pet, lying above the web 12, and actuating the switch 80. Accordingly, the controller 70 may be programmed to apply the PEMF pulse sequence in a one hundred percent duty cycle or some other duty cycle appropriate to accumulate the total proper amount within each day. In certain embodiments, the controller 70 includes clocks, timers, on and off actuators, delay selections, duration selections, and so forth. Thus, a user may program the controller 70 directly or indirectly through a computer or the buttons 72 and display 74 to select or prescribe a regimen. Thus, a system 10 in accordance with the invention is much more robust, flexible as to regimen, flexible as to control, and physically flexible as to its occasional user. Such characteristics have been unavailable in conventional prior art systems seeking to employ PEMF therapies.

One may think of the coils 50 embedded in each of the nodes 20 as sources 30 of PEMF pules establishing "shotgun points" around, and throughout a subject or even an appendage of a subject. For example, in the embodiment of FIG. 23, an entire subject may be exposed to an array of comparatively high intensity sources 30 in the nodes 20 all directed more or less upward into the subject "user."

In contrast, in the application embodied in FIG. 11, the micro-coils 50 within the nodes 20 are each directed in their own direction, normal (perpendicular) to a surface to which each is applied or is in contact. Thus, PEMF pulses may be irradiating the member from many different directions, and many different locations simultaneously. Such a bombarding of the member is done by intensified directed, electromagnetic flux. That flux is guided by the iron cores 40 within the coils 50. This intensity and direction provide increased effectiveness, direction, control, and specificity. For example, conventional mats or "rugs" of coils provide little guidance and no core as a guide for the lines of electromagnetic flux. Accordingly, such lines of flux immediately turn away from one another on each side or each face of the rug.

In contrast, the locations of cores 40, the proximity to the surface of a member or of the body of a user, and the multiple directions from which such a member is immersed or may be immersed, all contribute to higher intensities, better direction, and a normalization or evening out of the exposure.

In contrast, consider flux lines from a conventional PEMF mat or rug. Having no iron core to direct them, they pass through the center of such an oval, flat rug, and proceed to return back along paths almost parallel to the surfaces of the mat. This is the typical performance. Penetration into the member affected is minimal, and the amount of electromagnetic field propagated normal (perpendicular) to the surface of such a mat is a small fraction of the overall magnetic flux generated and propagated thereby.

Moreover, with the availability of widespread distribution of the micro-coils 50 in individual nodes 20 of the web 12 more than one axis of symmetry (think center line of the core and coil in an axially direction) may become available. In a conventional system, a single large mat provides one axis of symmetry, and thus one central location of maximum penetration, small though it may be. In contrast, the distributed nature of the nodes 20, each with its own micro-coil 50 and internal core 40 provides the same maximum direction and maximum strength for propagation as every other coil 50.

It is notable that the system 10 in accordance with the invention has been applied to soft tissue with remarkable results. Originally applying the invention and others related thereto to cases of bone density remediation or fracture remediation, Applicants discovered that soft tissue responds very well to the magnetic flux generated by the micro-coils 50. In fact, casting and otherwise immobilizing bodily members, such as feet and legs over a period of several weeks, such as the typical six to eight weeks required to heal a fracture, provided remediation of the atrophy in muscle tissues normally associated with immobilization and non-weight-bearing conditions.

In certain embodiments, pads may be formed as the pet bed 100, with more or less liner 104, padding 106, or both. In certain embodiments, liner material 104 placed on both sides of the web 12 and then a cover 102 over the entire outside thereof provides a mat that is suitable for comfortable relaxation thereon by a user. Typical pads 106 or liners 104 may be formed of viscous foam (e.g., "memory foam"), comparatively higher density urethane foam, or the like. In certain embodiments, a comparatively higher density urethane foam may actually be configured to have cut outs or apertures for receiving the nodes 20.

In other embodiments, such a comparatively stiffer foam and more dense foam may be configured in wedges to fit within the triangles formed by each of the runners 22 or connectors 22. In other embodiments, space may be excavated, or molded into a pad 106 in order to render a pad 106 substantially equally thick with the nodes 20. In such an embodiment, a comfortable layup of elastomeric foam liner material 104 may provide a system that is sufficiently and flexible, comfortable to be used as a pad under a user or over a user. In other embodiments, the cover 102, liner 104, and padding 106 may all be dispensed with, and the web 12 may simply be wrapped around a treatment location at will.

In certain embodiments, micro-coils 50 have been tested on users who are in conditions representing an effective twenty percent loss of mass in tissues per year. Upon exposure to micro-coils 50 in accordance with the invention, all users maintained their baseline cellular mass. This, in various experiments has been found to be the case in both bone cells and soft tissue cells.

Various sizes of webs 12 may be formed. Shapes may be configured somewhat arbitrarily for the individual direction, length, and so forth of each of the connectors 22 or runners 22 between the nodes 20. A rectangular, circular, hexagonal, or other polygonal shape may be formed. It has been found particularly acceptable to use a hexagonal shape illustrated in FIGS. 1 through 11 in order to provide a suitable spacing, and a straightforward connection scheme. Cross-sections of runners 22 may similarly be circular, triangular, square, other polygonal, semi circular, or the like.

As far as connection schemes are considered, one may begin the electrical circuit within the web 12 at any particular node 20. Accordingly, a corner node 20 of a polygon is a suitable place. Likewise, a node 22 intermediate two corners (vertices) of a polygon has also been found to be a suitable place. The circuit may then pass from that particular node 20 to an adjacent node 20. The path becomes a zig-zag or back-and-forth pattern up and down adjacent, parallel rows or columns of nodes 20.

However, in each row or drum of nodes 20, the wire 46 of the connector 22 does not pass all the way to the outer perimeter or periphery. Eventually, the connectors 22 must carry the wires 46, and specifically their conductors 47 along a pattern that will avoid back tracking through any particular leg 22 or connector 22.

That is, it not advantageous to have one of the connectors 22 be more stiff than another. The addition of multiple paths or wires 46, and particularly the metal conductors 47, through a single connector 22 would provide an increased stiffness. This is due to increasing the section modulus (a term of art specific to structural engineering and known in the art). With the hexagonal pattern, one may always develop a path that does not require more than a single wire 46 to be embedded within any connector 22, and thus no backtracking.

In a typical embodiment, the return path or the last legs of the electrical circuit may then pass through the unconnected peripheral nodes 20 to arrive back at the originating node 20 of the circuit. Thus, it is possible and it has been found suitable to connect all the nodes 20 into a single series connection in certain embodiments of an apparatus 10 in accordance with the invention.

In tests, pet owners have found that a web 12 embedded in a pet bed 100 as described hereinabove has provided relief for various ailments in dogs. Particularly, older, arthritic pets have been observed to become much more active, flexible, and able to increase movement and energy by sleeping on a pet bed 100 in accordance with the invention.

Soft tissue improvements in human patients have also been observed in experiments. For example, sprains, swelling, trauma, diabetic circulation issues, and the like often result in damage and subsequent inflammation in cells of soft tissue. In certain experiments, a user was observed to lose two inches of ankle diameter within two weeks. The swelling had originated in an ankle causing much pain, inflammation, and so forth.

As a practical matter, Applicants have considered the potential for interference between PEMF sources 30 in prior art inventions of Applicants. In observing experiments, Applicants have determined that the multiple iron cores 40 associated with the micro-coils 50 provide a wave guide with greater penetration, higher flux density, and yet full coverage and from multiple directions for an appendage or body. Spacing the nodes 20 at the selected distance, in the illustration about nine to twelve inches apart, may range from about four to about eighteen inches apart. A target distance is about ten inches.

Interference has been minimized because flux density has been concentrated right along the central axis of the coils 50 in each of the nodes 20. Thus, contrary to prior art attempts with coil mats, the flux density here is reversed, and is concentrated toward the central axis, rather than immediately concentrating around the surfaces of the flat coils of prior art systems. Meanwhile, since much less of the flux density is spread out away, there is less interference between the coils 50, which with their cores 40 operate as electromagnets.

Exercise is an interesting phenomenon. In recent years, exercise physiology has recognized the value of exercising all bodily members in multiple directions. That is, in some decades past, it has been common to develop exercise machines for improving a specific motion of a specific muscle or muscle group. However, modern exercise physiology has determined that the body may often be aided by maintaining the entire bodily core engaged in exercise by such activities as maintaining balance, free standing during exercise with various resistance mechanisms or weights, and so forth.

Applicants have determined that the operation of a system 10 in accordance with the invention appears to accord with exercise. Likewise, the multi-directional flux densities or directions of propagated flux densities provides, effectively, exercise in multiple directions. By suitable arrangement of the web 12 around a bodily member, one may effectively "exercise" a member even while that member is unloaded and stationary from a macroscopic viewpoint.

On a microscopic viewpoint, the cells are being exercised by the PEMF generated and propagated by each of the micro-coils 50. Thus, the observed conditioning of bone and muscle (in general, all tissues apparently) of a user occurs in response to the multi-directional nature of the bombardments from the nodes 20 of the web 12.

Thus, in general, the observed users experienced non-depredation of bone density and muscle mass, and enjoyed improvement in general health of the bodily members treated by the system 10 in accordance with the invention.

In the illustrated embodiments, Applicants have determined that treatment for chronic conditions, rather than acute conditions alone, may be effected by application of PEMF regimens to members or bodies of subjects. Because of the non-conservation-of-mass (or the flexibility and arbitrary arrangement) possible by a user arranging the web 12, various bodily members may be treated. Moreover, they may be treated from different angles on different occasions, different days, or different sessions. Meanwhile, chronic conditions, such as arthritis in pets appear to be remediated by use of the system 10.

Similarly, plantar fasciitis is a condition that results in substantial swelling and sensitivity of the nerves in bodily members. Plantar fasciitis is extremely painful and largely unresponsive, particularly in diabetics. In experiments with the system 10 in accordance with the invention, eight subjects out of eight test subjects were successful in overcoming inflammation due to plantar fasciitis.

Likewise, this micro-scale exercising of cells within a member or body by the PEMF of the micro-coils 50 appears to improve the adenosine tri-phosphate (ATP) levels in treated subjects. Such improved levels of ATP bode well for various health effects attributed to ATP, and reported in medical, scientific, nutritional, and other literature.

It has also noted that cancerous cells tend to be low in energy levels, and cells that are unhealthy tend to bunch up with one another. This results in a net decrease in surface area available for the transport processes of intake and outflow of materials (nutrients and wastes, oxygen, and so forth) across the surfaces of cells. That is, materials migrate through cell walls. To the extent that cells bunch up together, each covers a surface of another cell, thus denying each cell that much surface area available for the diffusion across the boundary of wastes, nutrients, and so forth.

In contrast, healthy cells tend to repel one another. The immersive, pulsed, magnetic flux from the micro-coils 50 appears to provide improved cell energy, less bunching, and thus improved cellular health.

The iron core 40 acting as a flux guide 40 for the micro-coil 50 permits point-controlled dosing. A particular joint may be positioned directly under one or more nodes 20 secured to the surface of a bodily member. Thus, point dosing at comparatively higher intensities than prior art systems is effected by the micro-coils 50 in the nodes 20 in web 12 in accordance with the invention.

The connection scheme of the nodes 20 in web 12 provides considerable dimensional stability in the hexagonal format. Enclosed triangular shapes are formed by adjacent connectors 22 or runners 22. Likewise, with the hexagonal configuration, the electrical wire circuit may escape from closed corners while connecting between adjacent nodes 20 the various coils 50. Applicants have tested various configurations and have not found anywhere that the hexagonal shape cannot access each node 20. Access is by one wire from any and all necessary directions, and no duplicate or backtracking conductors 47 or wires 46 traveling through connectors 22.

As a practical matter, the number of turns, voltage, current, and so forth passing through each coil 50 may be engineered to provide a suitable value of each. As a practical matter, the presence of iron cores 40 as flux guides has reduced the number of turns, the total voltage, and the amount of current required to provide the suitable amount of dosing of PEMF applied to a user.

As a matter of physical practicality, the tape switch 80 or contact switch 80 illustrated may be configured to be of any suitable length. However, it has been found that passing it completely across the center "diameter" of a web 12 assures that any body lying on top of the web 12 will properly engage the switch 80 and turn it on.

To accommodate movement of a pet, it has been found that a delay, such as from about five to about twenty seconds is appropriate before shutting off power to the web 12 upon the straightening (de-activation) of the switch 80. It has not been found necessary or appropriate to have any delay in onset of power to the web 12 upon activation of the switch 80. However, a range of from about five to about twenty seconds of delay, or more, may be useful, and ten seconds has been found suitable for most situations. This assures that a pet who moves about, will still be treated, yet the system 10 will shut off if the bed 100 is abandoned for movement to other locations or activities.

Likewise, the electrical connection suitable for the web 12 has been found easily handled by a plug 85 such as those commonly used in electronic and audio equipment. For example, a 2.5-millimeter-diameter standard plug on a cord 84 has been found suitable. A matching jack 26 embedded in a node 20 provides a suitable connection scheme. This provides for a minimum amount of tangling of cords 82, 84, 86 with the web 12. This also provides for simple dismantling of the system 10 and rolling up the web 12 with or without a cover 102. In fact, the web 12 may be folded in multiple directions, rolled, or the like.

As a matter of connection scheme, the switch 80, which may be referred to as a tape switch, tac switch, ribbon switch, or the like. It may be connected so as not to override the handset 70 or controller 70. Typically, the switch 80 operates as a communication device by opening and closing a circuit detected by the controller 70. Thus, the controller 70 may be configured to work with or without the switch 80.

In certain embodiments, tested in accordance with the invention, micro-coils 40 having approximately ninety three turns in twenty feet of wire 42 have been found suitable. Likewise, a connection of all the micro-coils 50 in series has been found suitable. In another embodiment, separate coils 50 individually constructed, and individually connected with individual wires may also serve. Typically, in construction, the wires 46 for the connectors 22 have been found to be suitable when formed of a copper, stranded wire of about twenty two gauge or less.

By pre-making the lengths of each, and the bare ends 48 of the conductors 47 therein, it has been found a straightforward matter to solder together the bare ends 44 of the magnet wires 42 with the bare ends 48 of the connector wires 46 in ready fashion. The iron core 40 may be cast as an insert in each spool 32, in order to avoid requiring any draft angle in molding. However, in other embodiments, the cores 40 may simply be inserted into the apertures 35 of the barrels 34 of the spools 32 and held there by the adhesive of a cover 52 or plate 52 serving as an insulator, securement, and electrical isolator for the bare ends 44, 48.

The controller 70 may connect to a computer wirelessly, or with a port, such as a USB port. However, it has not been found necessary. Meanwhile, the web 12 has been found to provide sufficient comfort when placed in a pad 106 or mass 106 of padding formed of chopped elastomeric foam such as is common in informal seating, pet beds 100, and the like.

In certain embodiments, a single hexagonal web 12 as illustrated in FIG. 23 may be suitable. In other embodiments, such as those of FIGS. 9 and 10, an extended hexagonal pattern has been found suitable. Over the top, a cover 102 has been found sufficient in many embodiments. If the web 12 is placed under a sheet, it is typically best placed under a memory foam liner and under the mattress cover in order to provide sufficient amelioration of the difference in density, stiffness, and shape that the nodes 20 and connectors 22 present.

The switch 80 provides a minimization of duty cycle by allowing programming of the controller 70 to simply operate until the total cumulative hours of treatment have been reached. The only reason to stop is not really safety but simply that there is no benefit beyond two hours of treatment per day. Thus, automatic dosing is available even though there is not a danger or damage to the patient nor to the device.

Bedridden patients may thus be provided protection in dosing automatically without manual intervention. Meanwhile, an individual seated or in bed incapable of personal movement control may simply apply the web 12 in any manner suitable, including over or around a particular bodily member for which treatment is desired.

Typically, the mold 60 is a single piece mold with open cavities and the substrate 54 is a vibrating table. Thus, high-density polyethylene, nylon, or the like may be used in forming the mold 60. Molds 60 do not need the complexities, costs, durability, heat-transfer capacity, etc. of metals, such as aluminum and steel.

The resin for the web 12 has been found to be robust. Strength, flexibility, dimension maintenance, and the like are all provided quite straightforwardly by a two-part, room-temperature-curing silicone composition. Meanwhile, such resins are available and may be specified with cure rates or times of from twenty minutes to about six hours.

The stranded wires 46 have been found to be sufficiently flexible powered by a voltage of about twenty four volts and three amps maximum on the power supply. A ten percent duty cycle is typical, but a user may control that duty cycle to be one hundred percent for a lesser time for the total amount. At current rates, a 72-Hertz system was originally developed but a 50 Hertz frequency has been found suitable in the web 12 in accordance with the invention. Ten percent of the wave form is "power on," with ten percent of the wave form "power off." Typically, at 50-Hertz, ten percent of each cycle is exposed to the application frequency, and the other ninety percent is simply idle.

It has been found that the efficacy of the system 10 in accordance with the invention is not improved above 50 Hertz. Although certain resonant frequencies may require other testing, and some argue that 7.2 Hertz is optimal, others argue that there is no optimum. Applicants have found that above the 50 Hertz frequency no additional benefit has been observed.

Thus, whereas laser therapy has been found useful, such devices cost thousands and tens of thousands of dollars. They require extensive training, protection for users and technicians, and so forth. In contrast, a system 10 in accordance with the invention is straightforward, simple to operate, provides no known negative side effects, and no inherent dangers to user or operator.

The present invention may be embodied in other specific forms without departing from its purposes, functions, structures, or operational characteristics. The described embodiments are to be considered in all respects only as illustrative, and not restrictive. The scope of the invention is, therefore,

What is claimed and desired to be secured by United States Letters Patent is:

1. An apparatus comprising:
   runners connected as a web to one another at vertices defining polygons of empty space between the runners, the runners being capable of arrangement corresponding to a plane, each runner is flexible to bend in multiple directions orthogonal to the length, both in and out of the plane; and
   nodes, each node being positioned as a vertex, of the vertices, interconnecting ends of at least two of the runners;
   the runners, each providing a corresponding and exclusive interconnection between adjacent nodes;
   each node containing an electromagnet comprising a micro-coil capable of generating a magnetic flux and surrounding a core capable of acting as a flux guide therefor, directing the magnetic flux normal to the plane along a central axis; and
   wherein the runners contain conductors electrically connecting the electromagnets to receive electricity.

2. The apparatus of claim 1, further comprising a controller operably connected to deliver the electricity to the nodes.

3. The apparatus of claim 2, programmed to dose the magnetic flux.

4. The apparatus of claim 3, wherein the nodes each have a surface positionable with respect to a member of a body of a subject.

5. The apparatus of claim 4, wherein the surface is positionable at an arbitrary angle corresponding to a skin surface of the subject.

6. The apparatus of claim 5, wherein the controller is programmed to pulse an electromagnetic field at a frequency selected to effect cellular exercise by generation of an electromagnetic flux in the member as a result of the electromagnetic field.

7. The apparatus of claim 6, wherein each runner is formed to bend in an arc having a radius selected to protect the conductor in each runner to resist mechanical failure.

8. The apparatus of claim 1, wherein:
   each node comprises at least one substantially flat surface parallel to the plane and positionable out of the plane;
   each runner is sufficiently flexible to position proximate a surface of a body of a subject;
   the nodes and runners form plurality of polygons defined by the runners as sides and the nodes as the vertices connecting the sides; and
   the apparatus comprises a controller operably connected to energize the micro-coils to control dosing by the electromagnetic field by controlling at least one of a frequency and a duration.

9. The apparatus of claim 1, further comprising a controller operable to provide a dosing regimen by pulsing an electromagnetic field at a frequency selected to be effective to obtain a cellular exercise response from a subject exposed to the electromagnetic flux resulting from the electromagnetic field.

10. The apparatus of claim 9, wherein:
    the frequency is from 7 to 70 Hertz; and
    the controller is operably connected to apply the electromagnetic flux at the frequency during a duty cycle, representing a percentage of time that the micro-coils are powered, from 5 to 90 percent.

11. A method for eliciting a response by at least one of tissues and cells in vivo, the method comprising:
    providing
        runners elongate and interconnected, at vertices to form a web of polygons defining empty space between the runners, the runners forming exclusive mechanical and electrical connections between vertices of the polygons, and corresponding to a plane, each runner extending a sufficient length, and each runner is flexible to bend in multiple directions, transverse to each runner's length, in and out of the plane, and
        nodes, wherein each node is positioned as a vertex, of the vertices, interconnecting ends of at least two of the runners, the runners providing exclusive interconnections between the nodes,
    wherein each node further contains an electromagnet comprising a micro-coil, surrounding a core and capable of generating a magnetic flux in said core acting as a flux guide therefor, each core directing the magnetic flux normal to the plane along a central axis thereof and not relying on any interaction with any other node, and each runner contains a conductor electrically connecting the electromagnets in adjacent nodes to receive electricity thereto;
    positioning the electromagnets to conform arbitrarily to a body of a subject by positioning the nodes by flexing the runners;
    selectively controlling power to the electromagnets; and
    directing the magnetic flux by concentrating along the central axis of each core.

12. The method of claim 11, further comprising directing the magnetic flux into living cells, said cells selected from bone cells and muscle cells.

13. The method of claim 11, further comprising providing a controller, said controller activating the electromagnets according to a pre-determined pulsing regimen.

14. The method of claim 13, further comprising:
    selecting a member of the subject;
    positioning the nodes proximate a surface of the member; and
    exposing the member to an electromagnetic field guided by the cores.

15. The method of claim 13, wherein the subject is selected to be a mammal.

16. The method of claim 11, wherein the runners and nodes are formed into the web of polygons formed by the runners, wherein the nodes form the vertices thereon.

17. The method of claim 11, further comprising placing at least some of the nodes in an orientation rendering the central axis to be at least one of parallel and tangent to the subject.

18. The method of claim 11, further comprising positioning the nodes about a member of the subject by bending the runners "out of plane" with respect to the plane to orient a plurality of the nodes at unique angles with respect to one another.

19. The method of claim 11, wherein:
    the runners and nodes comprise a homogeneously molded, elastomeric polymer;
    the nodes and runners are formed into the web of polygons defining empty space therewithin; and
    the runners define sides and the nodes define the vertices of the polygons.

20. A method comprising:
providing electromagnets, each electromagnet comprising a wire wrapped around a core of iron to generate an electromagnetic field not engaged with that of another electromagnet;
providing runners arranged in a web defining polygons of empty space within the runners forming exclusive mechanical and electrical connections between the electromagnets;
arranging the runners as sides and the electromagnets as nodes acting as vertices in the web; and
positioning the nodes of the web on a subject in a deployed configuration by wrapping the runners in arbitrary directions with respect to a plane corresponding to the web in an unapplied configuration.

* * * * *